United States Patent [19]

Nusbickel, Jr et al.

[11] Patent Number: 4,470,304
[45] Date of Patent: Sep. 11, 1984

[54] ULTRASONIC INSPECTION SYSTEM

[75] Inventors: Edward M. Nusbickel, Jr, Allentown; Charles J. Romberger, Coopersburg; Glenn L. Hunsicker, Allentown, all of Pa.

[73] Assignee: Bethlehem Steel Corp., Bethlehem, Pa.

[21] Appl. No.: 383,657

[22] Filed: Jun. 1, 1982

[51] Int. Cl.³ ............................................ G01N 29/04
[52] U.S. Cl. ........................................ 73/611; 73/626; 73/1 DV
[58] Field of Search ................. 73/611, 612, 613, 614, 73/615, 609, 610, 1 DV, 620, 625, 626, 631, 628, 644; 364/507

[56] References Cited

U.S. PATENT DOCUMENTS

| | | | |
|---|---|---|---|
| 3,481,186 | 12/1969 | Cellitti et al. | 73/612 |
| 3,616,684 | 11/1971 | Nusbickel, Jr. | 73/641 |
| 3,672,210 | 6/1972 | Cressman et al. | 73/612 |
| 3,872,715 | 3/1975 | Pittaro | 73/611 |
| 3,942,358 | 3/1976 | Pies | 73/611 |
| 3,981,184 | 9/1976 | Matay | 73/609 |
| 3,986,389 | 10/1976 | Mesina et al. | 73/611 |
| 4,033,179 | 7/1977 | Romrell | 73/612 |
| 4,088,028 | 5/1978 | Hildebrandt | 73/611 |
| 4,173,897 | 11/1979 | Forstermann et al. | 73/611 |
| 4,173,898 | 11/1979 | Forstermann et al. | 73/611 |
| 4,205,553 | 6/1980 | Rudis et al. | 73/611 |

Primary Examiner—Stephen A. Kreitman
Attorney, Agent, or Firm—John J. Selko

[57] ABSTRACT

Multi-channel automatic on-line ultrasonic inspection system for real time high-speed pulse echo testing is done across the width of a hot moving workpiece, such as steel plates and the like. In addition to a multiplexed transducer array search unit, the system includes an adjustable ultrasound fluid couplant, a main ultrasonic instrument modified with a digital multi-channel R.F. attenuation controller and a digital automatic flaw gate controller combined as on-line calibration means. The calibration means automatically corrects echo pulses for attenuation errors due to effects of variations in workpiece alloy or composition and temperature, and timing errors due to effects of variations in thickness and transducer gap, respectively. System further includes an ultrasonic data buffer/controller (UDBC) for digitizing, encoding and storing corrected or uncorrected flaw area data passed by the flaw gate during workpiece movement. The UDBC, together with a process control minicomputer, a display terminal and printer, provides computer-aided flaw area detection and reconstruction with printouts of an encoded flaw map and an A.S.T.M. flaw evaluation.

22 Claims, 8 Drawing Figures

PLATE INSPECTION FLAW MAP

DATE:   TIME:   PLATE #

PLATE DIMEN   1/2" x 74" x 144"   TEMP 350° F.

CHANNEL NUMBER

| SCAN | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|
| 1 |   | 2 |   |   |   |   |   |   |   |    |    |    |    |    |    |    |
| 2 |   |   |   |   |   |   | 2 |   |   |    | 2  |    |    |    |    |    |
| 4 |   |   |   |   |   |   |   |   |   |    | 2  |    |    |    |    |    |
| 5 |   |   |   |   |   |   |   |   |   |    | 2  |    |    |    |    |    |
| 6 | 2 |   |   |   |   |   |   |   |   |    |    |    |    |    |    | 2  |
| 7 |   | 2 |   |   |   |   |   |   |   |    |    |    |    |    |    |    |
| 8 |   | 2 | 2 |   |   |   |   |   |   |    |    |    |    | 2  |    |    |
| 9 |   | 2 |   |   |   |   |   |   |   |    |    |    |    |    |    |    |
| 10 |  | 2 |   |   |   |   |   | 2 |   |    |    |    |    |    |    |    |
| 12 |  |   | 2 |   |   |   |   | 2 |   |  2 |    | 2  | 2  |    |    |    |
| 13 | 2 | 2 |   |   |   | 2 |   |   |   |    |    | 2  |    |    |    |    |
| 14 |  |   | 2 | 2 | 2 |   |   |   |   |    |    |    |    |    |    |    |
| 15 | 2 |   |   | 2 |   |   |   |   |   |    |    |    |    |    |    |    |
| 16 |  |   |   | 2 | 2 | 2 |   |   |   |    |    |    |    |    |    |    |
| 68 |  |   |   |   |   |   |   |   |   |    |    | 1  |    |    |    |    |
| 70 |  |   |   |   |   |   |   |   |   |    |    | 1  |    |    |    |    |
| 72 |  |   |   |   |   |   |   |   |   |    |    | 1  |    |    |    |    |
| 207 |  |   |   |   |   |   |   |   |  |    |    |    |    |    |    | 1  |
| 208 |  |   |   |   |   |   |   |   |  |    |    |    |    |    |    | 1  |
| 210 |  |   |   |   |   |   |   |   |  |    |    |    |    |    |    | 1  |
| 211 |  |   |   |   |   |   |   |   |  |    |    |    |    |    |    | 1  |
| 212 |  |   |   |   |   |   |   |   |  |    |    |    |    | 2  |    |    |
| 213 |  |   |   |   |   |   |   |   |  |    |    |    |    | 2  |    | 1  |
| 1069 |  |   |   |   |   |   |   |  |  |    |    |    |    |    |    | 2  |
| 1070 |  |   |   |   |   |   |   |  |  |    |    | 1  |    |    |    | 2  |
| 1071 |  |   |   |   |   |   |   |  |  |    |    |    |    |    |    | 2  |
| 1082 | 1 | 2 | 2 |  |   |   |   |  |  |    | 2  |    | 2  |    |    |    |
| 1093 | END OF PLATE | | | | | | | | | | | | | | | |

FIG. 7

PLATE    INSPECTION    EVALUATION    (ASTM A-578)

DATE:          TIME:                    PLATE #

PLATE DIMEN   1/2" x 74" x 144"    TEMP 350° F.

SCAN
6  >
10         ASTM A-578  LEVEL I  FLAWED

17 >
67         ASTM A-578  LEVEL I  CLEAR

73 >
206        ASTM A-578  LEVEL I  CLEAR

210 >
213        ASTM A-578  LEVEL I  FLAWED

214 >
1068       ASTM A-578  LEVEL I  CLEAR

1072 >
1081       ASTM A-578  LEVEL I  CLEAR

1082 >     ASTM A-578  LEVEL I  FLAWED

1083 >
1093       ASTM A-578  LEVEL I  CLEAR

1093   END OF PLATE

ULTRASONIC INSPECTION SYSTEM

BACKGROUND OF THE INVENTION

This invention relates to a computer-based multi-channel automatic on-line ultrasonic inspection system for real time testing of a hot movable workpiece, such as steel plates and the like, which is corrected for one or more error-causing variable test conditions, and further includes computer-aided flaw area detection and multi-level reconstruction means for causing printouts of a flaw area map and a flaw evaluation.

DESCRIPTION OF THE PRIOR ART

Contemporary steel mills, for example, roll hot steel plates of various alloys or compositions in a variable thickness range of about 6.35 to 76.2 mm. (0.25" to 3.0"), at widths up to 4,064 mm. (160"), and at variable speeds up to 183 m.p.m. (600 f.p.m.). After rolling, hot steel plates are normally spray cooled to 205° C. (400° F.) and lower as they are conveyed through marking and inspection stations at rolling speeds. Troublesome production delays sometimes occur which cause further cooling and a temperature change to the rolled plate before, during or after arriving at the inspection station. An additional inspection problem arises because many plates experience waviness, yet are subject to the same test accuracy requirements for internal quality as are generally flat plates produced at rolling speeds.

Ultrasonic pulse echo testing techniques are well known nondestructive methods of determining the internal quality of a variety of products, including the hot rolled steel plate exemplified herein. Heretofore, one commonly used ultrasonic testing method of plate inspection was done off-line after the plate cooled, rather than on-line with hot plate as is required herein. Typical commercially available ultrasonic inspection apparatus includes a portable multi-channel ultrasonic transducer array acoustically coupled with an ultrasound fluid to the cooled steel plate supported by a bed. Said array is multiplexed to a single-channel main ultrasonic instrument having a CRT display. The CRT displays a preselected channel of front and back surface pulse echo signals, and a flaw pulse echo signal therebetween if an internal flaw is present in the plate. A multi-channel strip chart analog recorder produces a flaw record of each transducer channel used in the inspection path traversed by said array, which record must be interpreted by a trained inspector.

The typical commercially available ultrasonic inspection apparatus requires manual adjustments by the trained inspector of R.F. gain and db. attenuation of each sequence of front, flaw and back echo pulse signals when each product of differing alloy or composition and/or temperature is inspected since these variable parameters affect transducer-detected attenuation errors. Similarly, manual adjustments must be made of front, flaw and back echo gate time delay when each product of differing thickness and/or transducer gap due to waviness is inspected since these variable parameters affect transducer-detected timing errors. All such manual adjustments and variations thereto must be made while the hot rolled plate is moving along an inspection path at the aforesaid speed. Each inspector must also be trained to interpret and evaluate the pulse echo amplitude and flaw timing data of each single-channel sequence displayed on the CRT in order to make a subjective determination of acceptance or rejection of the plate internal quality at a finite area.

It will be readily apparent that the manually-adjusted typical commercially available ultrasonic testing method and apparatus used off-line is not an acceptable approach to solving the on-line inspection requirements of hot steel plate rolled under the aforesaid variable speed and test conditions. Generally, there are no provisions for measuring plate temperature and adjusting acoustical couplant cooling to a predetermined effect when hot plate temperature is above room temperature. Further, production line speeds are too rapid to employ manual adjustments during testing for correcting the aforesaid transducer-detected attenuation and/or timing errors. Furthermore, there are no provisions for high-speed automatic interpretation and evaluation of every flaw echo pulse signal to avoid a subjective determination and interpret classification of plate defects through observation in the CRT display by the inspector.

Attempts have been made in other apparatus to automate the flaw gate range adjustment on-line to simply accommodate some degree of variations in plate thickness without considering the remaining variables causing echo pulse errors. Little success has been achieved with this arrangement in an overall inspection system approach. Other proposals have been suggested for so-called automatic on-line ultrasonic inspection systems, presumably computerized, which require that plate thickness be measured by a detector upstream from an array of flaw-detecting transducers at an inspection station, and somehow compensate a flaw gate for plate thickness variations. Details on such proposals are not readily available. However, it is believed such proposed systems require a substantial amount of input/output operations and arithmetic calculations that must be performed by a process control type computer.

Thus, none of the known prior art ultrasonic testing and inspection systems have been entirely satisfactory for use on-line in a contemporary steel mill where steel plate is rolled under the aforesaid variations in test conditions and production speeds, yet provide a real time interface with a digital process control type computer for simplified analysis of flaw area defects.

SUMMARY OF THE INVENTION

A main object of this invention is to overcome the foregoing difficulties and shortcomings of the prior art apparatus.

Another object of this invention is to provide an improved automatic on-line ultrasonic inspection system for real time testing of a hot moving workpiece such as steel plates and the like.

Still another object of this invention is to provide the foregoing improved automatic on-line ultrasonic inspection system with the capability of automatic, rather than manual, calibration for error-causing effects of variations in workpiece alloy or composition, temperature, thickness and/or transducer gap, as well as workpiece position.

Another object of this invention is to provide the foregoing improved automatic on-line ultrasonic inspection system with the capability of high-speed flaw detection across the width of the hot moving workpiece, yet simplify interfacing with computer-aided flaw area reconstruction at variable workpiece speed and position, and printout flaw maps and flaw evaluations.

Still another object of this invention is to provide an improved automatic on-line ultrasonic inspection system having self-diagnostic features, yet is readily maintainable by mill operating personnel.

The foregoing objects and advantages may be obtained by incorporating into new or existing hot steel plate rolling mills, and the like, an improved on-line ultrasonic inspection system for real-time automatic determination of area defects in a flat workpiece, said workpiece movable at a variable speed along an inspection path and which may be subject to one or more error-causing test condition variables, including attenuation-error causing variations in workpiece alloy or composition and/or temperature, and timing-error causing variations in workpiece thickness and/or transducer gap caused by workpiece waviness. The improved ultrasonic inspection system is provided with a multi-channel ultrasonic transducer array search unit having a sequence of echo pulses for each channel multiplexed through a mill remote terminal, the search unit operating with an adjustable ultrasound fluid couplant varied according to cooling effect needed as determined by plate measured temperature and speed. Also provided is a modified main ultrasonic instrument operatively associated with echo pulse signals from the search unit array and on-line calibration means having respective attenuation and flaw gate range controller means for high-speed automatic correction of transducer-detected attenuation and timing errors in each said sequence of echo pulses, thereby obviating the aforesaid necessity of manual adjustments to the ultrasonic instrument whenever a variation in workpiece test condition occurs. The system is further provided with corrected flaw data digital processing means having means for sensing workpiece position relative a transducer array search unit, and an ultrasonic data buffer/controller (UDBC) for digitizing, encoding and storing corrected or uncorrected flaw area data passed by the flaw gate during workpiece movement and tracked by the position sensing means. The UDBC acts as a real time interface which, together with a process control minicomputer, a display terminal and a printer, provides the system with computer-aided flaw area detection, analysis, and reconstruction means having printouts of an encoded flaw area map and an A.S.T.M. flaw evaluation. Self-diagnosis capabilities are incorporated in the system and are provided in part by preset switches and displays associated with the automatic attenuation controller, the automatic flaw gate controller and the digital ultrasonic data buffer/controller, and also in part by the minicomputer programmed by the display terminal.

BRIEF DESCRIPTION OF THE DRAWINGS

FIG. 7 is an illustration of a computer printout of a flaw map of the present invention.

FIG. 8 is an illustration of a computer printout of an A.S.T.M. flaw evaluation of the present invention.

DESCRIPTION OF THE PREFERRED EMBODIMENTS

Figure 1:
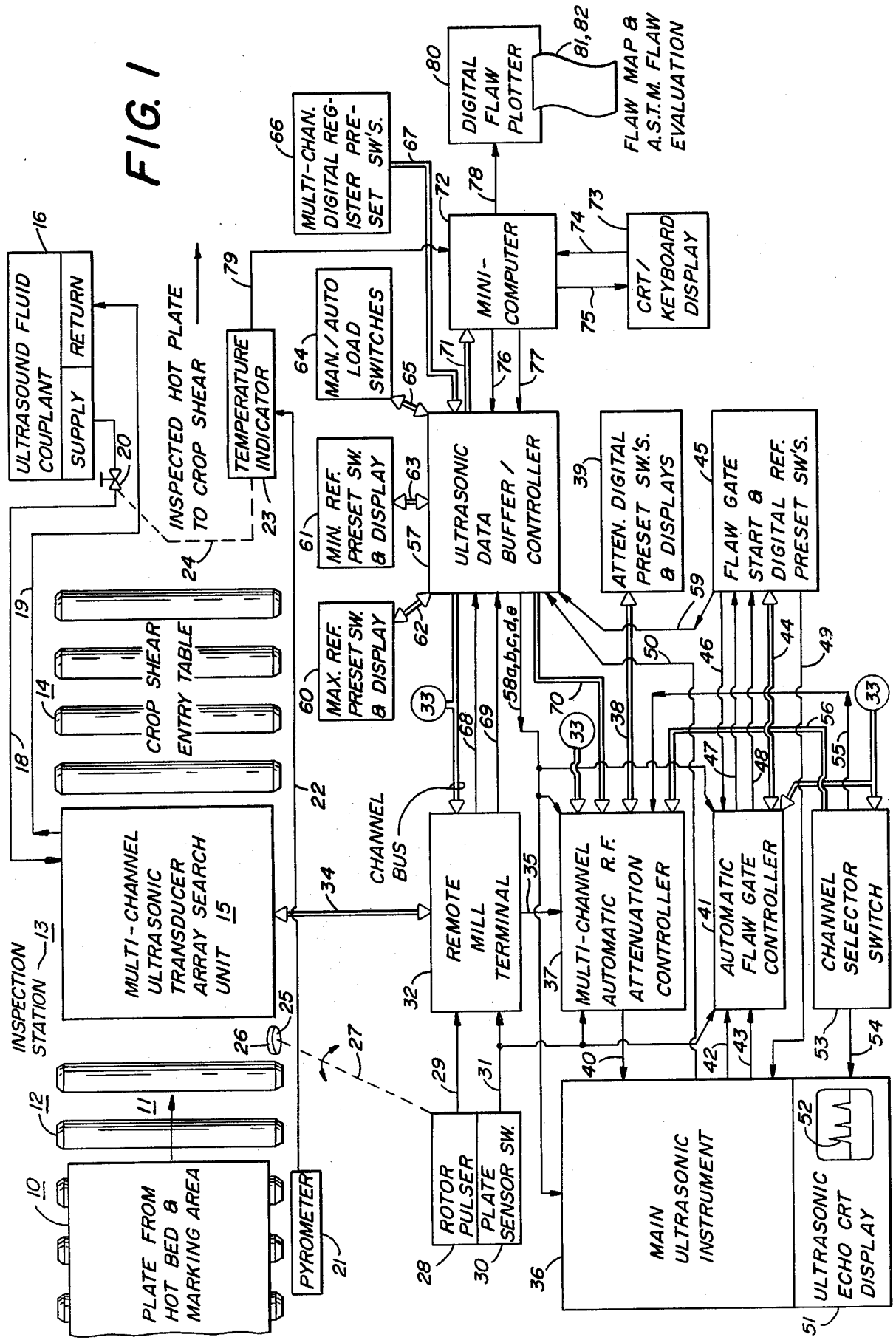
FIG. 1 is a block diagram of the present invention showing an automatic on-line ultrasonic inspection system incorporated in, for example, a hot rolled steel plate mill.

Referring to the drawings, particularly FIGS. 1-6, there is shown the improved ultrasonic inspection system for determining area defects in a flat hot rolled workpiece, such as plate 10, movable at a speed of up to 183 m.p.m. (600 f.p.m.) along an inspection path 11 in the direction shown by an arrow in FIG. 1. Plate 10 in the present invention is subject to any one or more error-causing variable test conditions. These are exemplified as plate alloy or composition within limits, temperature at about 205° C. (400° F.) and below, thickness 6.35 to 76.2 mm. (0.25" to 3.0") at widths up to 4,064 mm. (160"), and/or transducer gap caused by plate waviness, all plate properties occurring either initially or varying somewhat edgewise and/or lengthwise at plate rolling speeds.

Hot plate 10, after hot rolling, is moved along inspection path 11 from hot bed and marking area 12, through inspection station 13 and subsequently to crop shear entry table 14. Here plate 10 is prepared to be cut by a crop shear (not shown) into pieces sized according to input order data and flaw area information provided by the improved ultrasonic inspection system, or the inspection system as will be referred to hereafter.

Located at inspection station 13 is one part of multi-channel ultrasonic pulse echo tester means including multi-channel ultrasonic transducer array search unit 15, or simply search unit 15, extending laterally across hotplate 10 and having one transducer for each lateral incremental area of the plate to be inspected. Search unit 15 is preferably located under hot plate 10 as the plate moves along inspection path 11 so as to have a clear and unobstructed top surface required by many rolling mill operating and maintenance personnel. When desired, search unit 15 may be of the type disclosed in co-pending patent application "Ultrasonic Transducer Suspension System for On-Line High-Speed Ultrasonic Inspection of Flat Rolled Products", Ser. No. 264,390, filed May 18, 1981, now U.S. Pat. No. 4,375,167, by the same assignee.

If a hot plate 10 top side ultrasonic inspection method is desired, an alternative search unit 15 may be used as disclosed in U.S. Pat. No. 3,616,684, "Ultrasonic Inspection Carriage" assigned to the same assignee. The push handle therein may be replaced with a pivotal mechanism to raise and lower the inspection frame relative hot plate 10 movement along inspection path 11. Both preferred and alternative search units 15 incorporate therein transducer suspension means for following hot plate 10 waviness so as to minimize but not eliminate variation in transducer gap.

Both preferred and alternative search unit 15 embodiments need a source of ultrasound fluid couplant 16 to provide a flow of acoustical couplant 17 over supply line 18 between search unit 15 transducers and either the underside or top side of hot plate 10, respectively. In the preferred embodiment of search unit 15, for example, spent fluid is collected and returned over return line 19 back to source 16 for reuse, otherwise it may be discarded. In mill operations where hot rolled plate 10 is to be inspected at temperatures of 205° C. (400° F.) and above, the capability of source 16 is increased. Fluid supply valve 20 is placed in supply line 18 to control fluid flow for a predetermined localized plate cooling effect sufficient to conduct an inspection at the transducer array in search unit 15.

The amount of localized cooling required to take place at a given production speed is determined by measuring hot plate 10 temperature with pyrometer 21 located in area 12 before inspection station 13 and sending the resulting hot plate temperature signal over line 22 to temperature indicator 23. An inspection station 12 operator, when reading plate temperature indicator 23, adjusts fluid supply valve 20 to a known value related to workpiece surface cooling and effect to temperature on acoustical coupling only. Alternatively, device 23 may be a temperature indicator/controller which, via dotted line 24 in FIG. 1, will automatically control valve 20 to perform the same function as the aforesaid inspection station operator. Further, hot plate 10 production speed may vary during rolling, or even come to rest at times, this giving rise to additional situations requiring corresponding adjustments to fluid control valve 20. Moreover, the acoustical couplant 17 cooling effect may not be sufficient to prevent all attenuation errors detected by the array of transducers in search unit 15. There may still be some attenuation error attributed to plate 10 internal temperature as will be discussed below.

Hot plate 10 may move in either of opposite directions along inspection path 11 during some rolling mill operations, but normally moves downstream from marking area 12 through inspection station 13 as shown in FIG. 1. Hot plate 10 movement is tracked in both directions by wheel 25 having surface 26 engaged with plate 10 and a rotatable shaft 27 to drive rotor pulser 28. Rotor pulser 28 generates a position signal on line 29 which represents plate 10 location at each lateral incremental area tested along inspection path 11. Wheel shaft 27 is also adapted to move down and up to detect respective presence and absence of hot plate 10. Shaft 27 up/down movement activates plate sensor switch 30 and outputs a plate presence-absence signal on line 31. The presence-absence signal is used to synchronize control logic in electronic component in the present ultrasonic inspection system.

Another part of the multi-channel ultrasonic pulse echo tester means is remote mill terminal 32 located a short distance off-line at inspection station 13. Remote mill terminal 32 includes multi-channel R.F. pulser/receiver circuit means, shown in FIG. 2, to be multiplexed in response to transducer scanning signals on channel bus 33. This circuit means causes each ultrasonic transducer in search unit 15 to transmit an R.F. pulsed beam into hot plate 10 and receive reflected echo beams therefrom over multi-channel R.F. signal cable 34. Multi-channel cable 34 is as short as practical to minimize R.F. signal attenuation and installation costs. Thus, multi-channel cable 34 carries a multiplexed sequence of front, flaw and back echo pulses, one sequence for each transducer channel output from the array in search unit 15, to remote mill terminal 32. Also included in the circuit means of remote mill terminal 32 are multi-channel receiver preset gain adjusters, one for each transducer channel, which equalize the R.F. echo pulse gain of each channel regardless of individual channel characteristic variations up to this point in the inspection system. The multiplexed transducer scanning means causes remote mill terminal 32 to output any one sequence of R.F. front, flaw and back echo pulses having an equalized preset gain on single channel output line 35. However, each sequence of echo pulses, whether input on multi-channel input cable 34 or output on single channel output line 35, may be subject to the aforesaid one or more sources of transducer-detected attenuation and/or timing errors.

Figure 2:
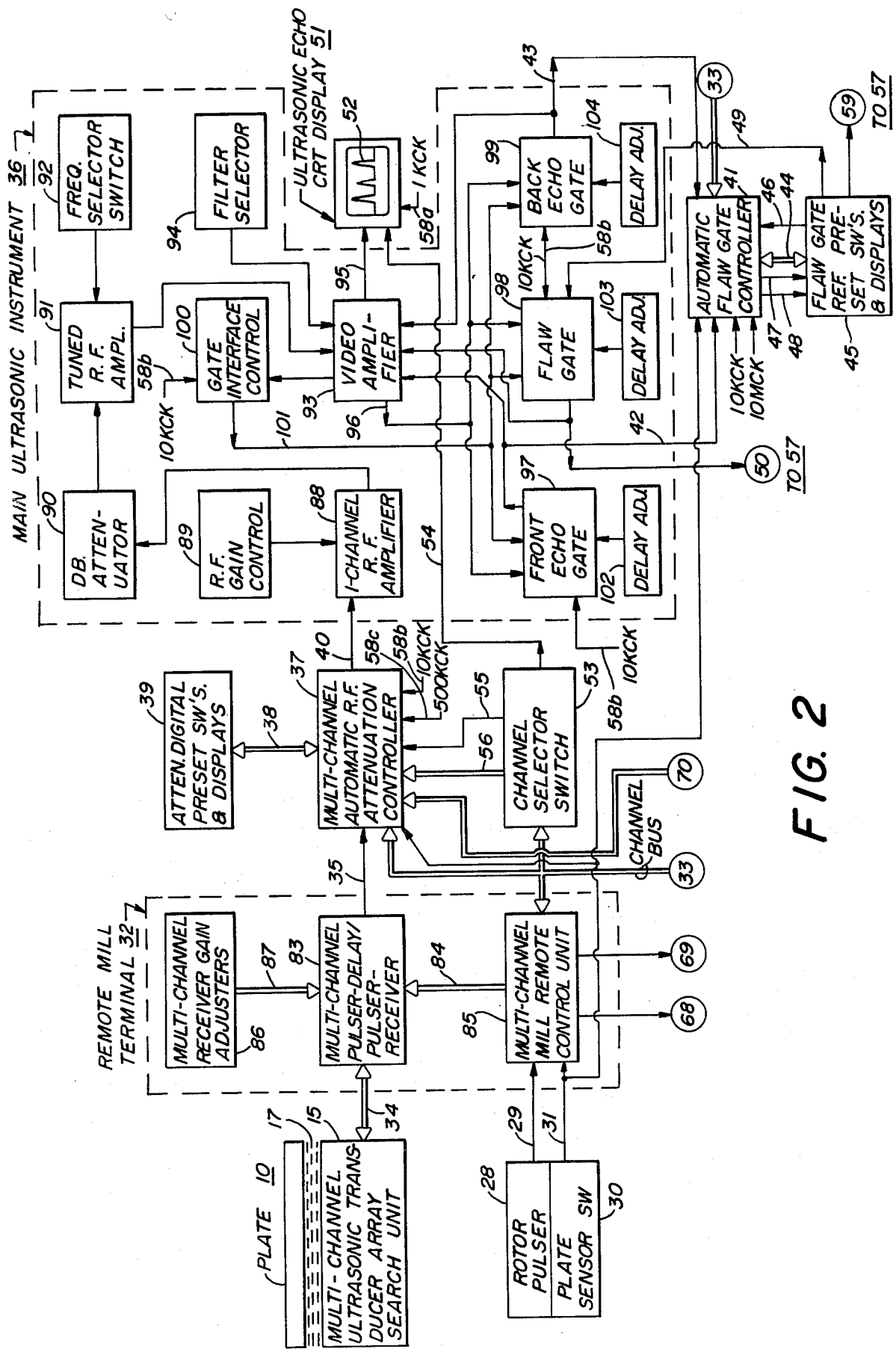
FIG. 2 is a block diagram of the transducer array-to-ultrasonic instrument portion of the automatic on-line ultrasonic inspection system of the present invention.
Figure 3:
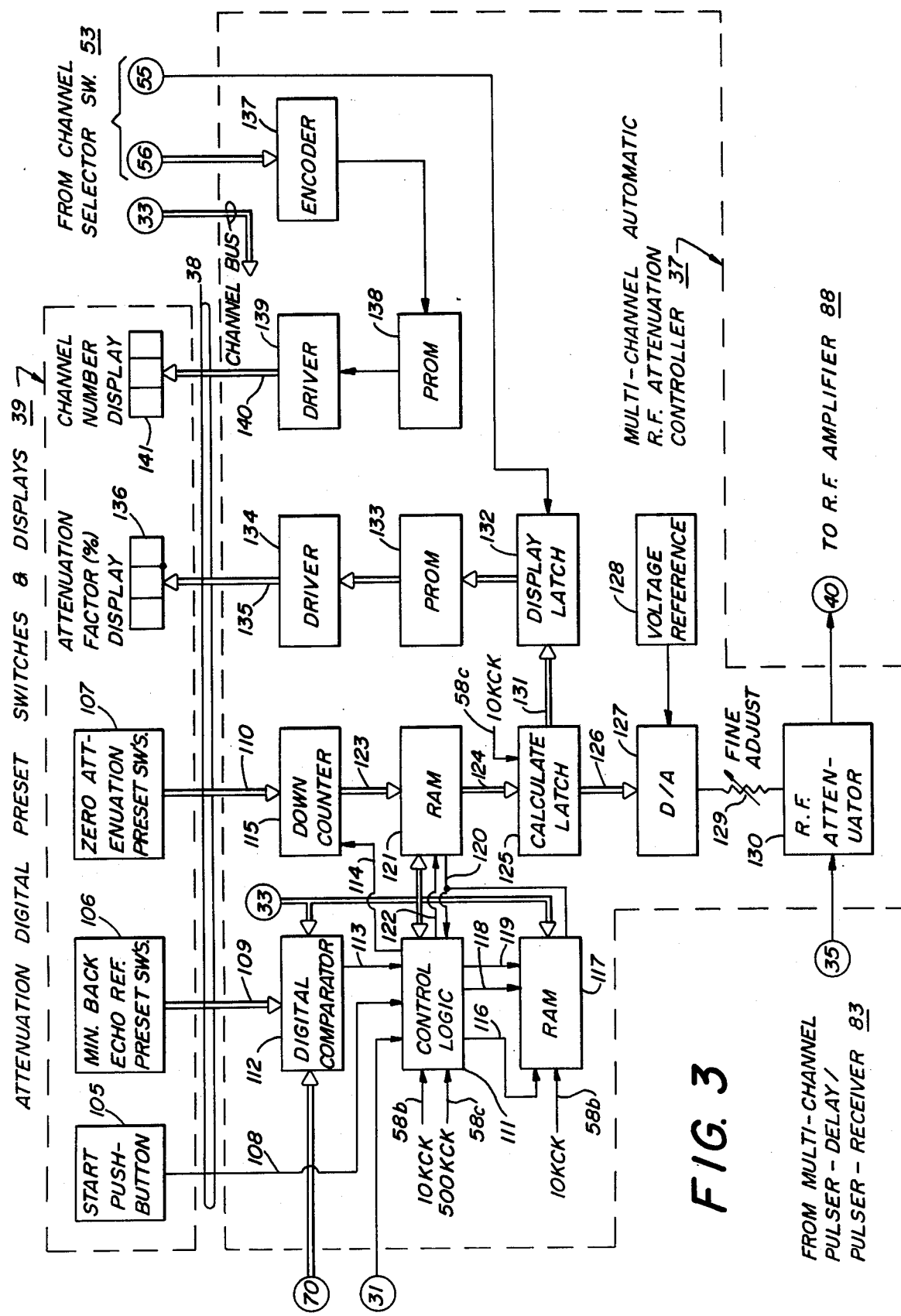
FIG. 3 is a block diagram of a multi-channel automatic R.F. attenuation controller portion of the calibration means referred to in FIG. 2.

The improved ultrasonic inspection system shown in FIG. 1 and partically in FIG. 2 includes calibration means for correcting R.F. pulse echo attenuation and/or timing errors that may be present in the sequence of echo pulses on single channel output line 35. The calibration means includes one or two respective controller means adapted to operate with a modified main ultrasonic instrument 36, such as Branson Model 303, to correct either or both types of echo pulse errors, if desired. When operating conditions are such that any transducer in the array in search unit 15 is subjected to a test condition variation in plate 10 alloy or composition and/or temperature, as is detected in actual practice, then the first or digital multi-channel automatic R.F. attenuation controller means 37 is provided for automatically correcting attenuation errors as shown in FIG. 3 described below. Multi-channel attenuation controller means 37 is synchronized by the plate presence-absence signal on line 31 and acts in response to each multiplexed sequence of said echo pulses input on line 35, and a present reference signal input on line 38 from preset and display device 39. Attenuation controller means 37 acts to vary preset output gain thereof proportional to attenuation error of each pulse echo sequence from every transducer in the array of search unit 15. Attenuation error corrected echo pulse sequence for one channel at a time is output from controller means 37 over line 40 to a modified R.F. input of main ultrasonic instrument 36.

Figure 5:
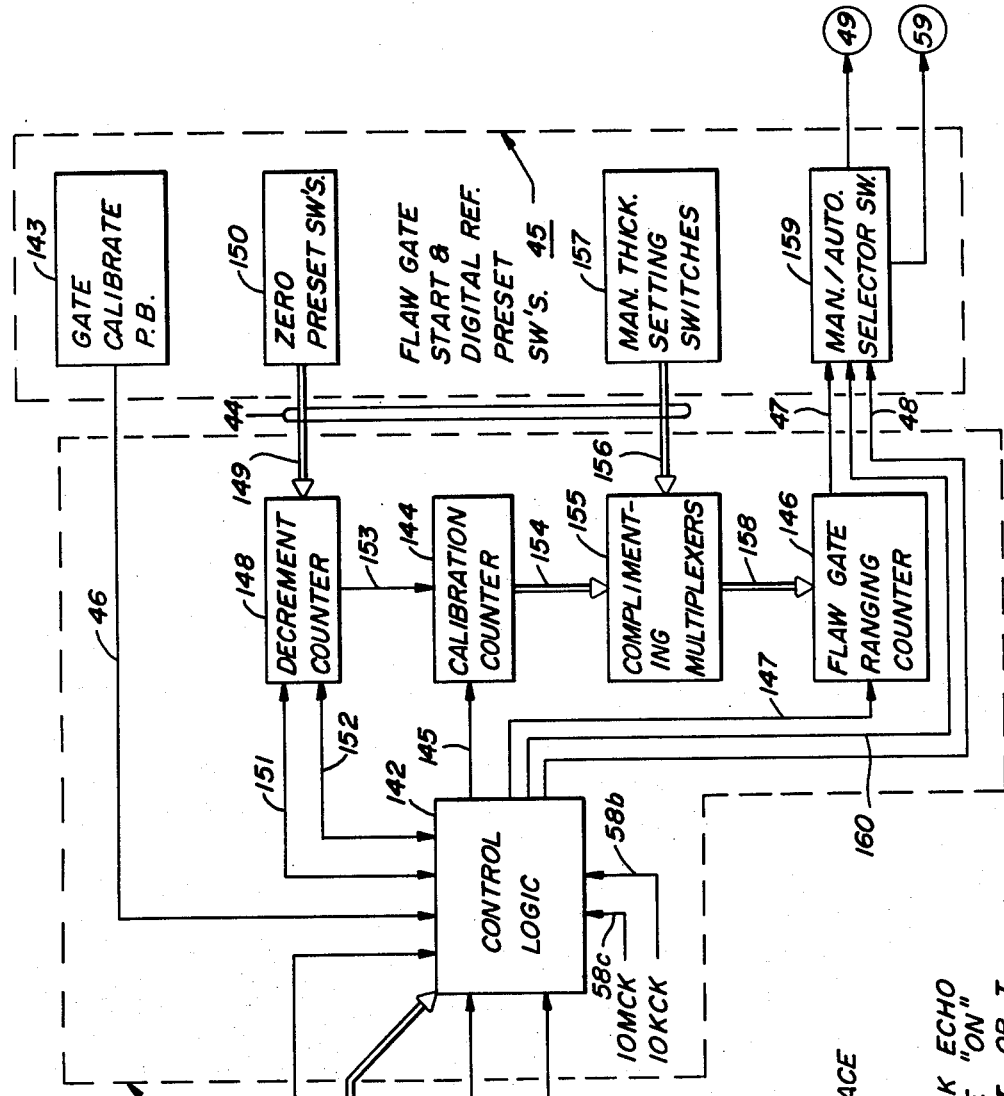
FIG. 5 is a block diagram of an automatic flaw gate controller portion of the calibration means associated with the ultrasonic instrument shown in FIG. 2.
Figure 4:
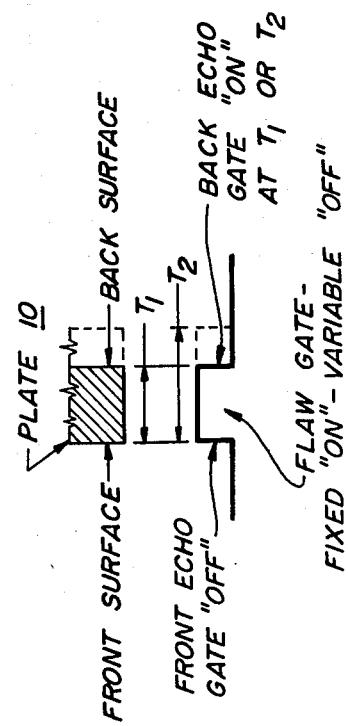
FIG. 4 is a diagram of how plate thickness variations cause variations in back echo gate "off" position.

When operating conditions are such that any transducer in the array in search unit 15 is subjected to a test condition variable in hot plate 10 thickness or associated transducer gap, as is also detected in actual practice, than the second or digital automatic flaw gate range controller means 41 is provided for automatically correcting each flaw echo timing error as shown in FIGS. 4 and 5 described below. Flaw gate range controller means 41 is synchronized with the plate presence-absence signal on line 31 and acts in response to each sequence of front and back echo pulses on lines 42, 43, preset reference signals input on cable 44 from flaw gate start and preset device 45, and a calibration start signal on line 46. Flaw gate range controller means 41 generates a variable flaw gate off-time signal associated with a multiplexed transducer which is fed over line 47 along with a back echo pulse on line 48, to device 45. Device 45 makes a manual or automatic selection of the flaw gate off-time signal and feeds it over line 49 in a feedback loop to a modified flaw gate in the output of main ultrasonic instrument 37. In this manner, manual or automatic timing-error corrected flaw echo pulses are output one per sequence from main ultrasonic instrument 37 over line 50.

When operating conditions are such that transducer-detected test condition variables in hot plate 10 cause both the attenuation and timing errors, then the improved ultrasonic inspection system calibration means includes both digital multi-channel automatic R.F. attenuation controller means 37 and digital automatic flaw gate range controller means 41 operatively associated with modified main ultrasonic instrument 36 as described above. In this manner, both controller means 37, 41 cause modified main ultrasonic instrument 36 to output on line 50 each echo pulse sequence with attenuation-error corrected front, flaw and back echo pulses, and a timing-error corrected flaw echo pulse.

The modified main ultrasonic instrument 36 is equipped with ultrasonic echo CRT display 51 where video trace 52 of a single channel sequence of corrected or uncorrected front, flaw and back echo pulses is observed. One of the multiplexed transducer channels on channel bus 33 is established by channel selector switch 53 outputting that channel number signal on line 54 to CRT display 51 and on line 55 to attenuation controller means 37. Channel selector switch 53 also outputs a digital multi-channel signal on cable 56 to attenuation controller 37 where this signal, together with the single-channel signal on line 55 to CRT display 51, are used as described below.

Figure 6:
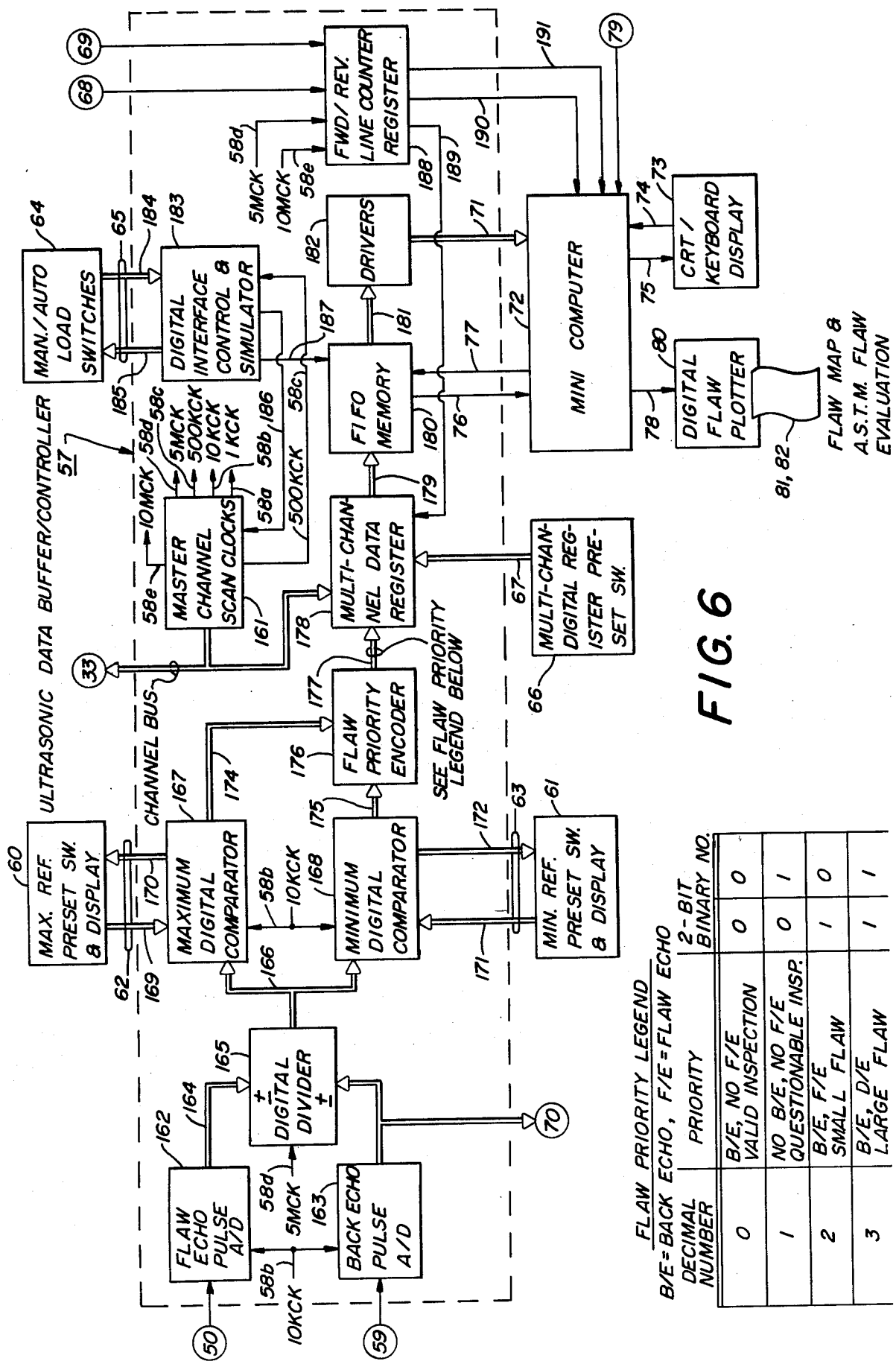
FIG. 6 is a block diagram of the remaining portion of the FIG. 2 system shown the ultrasonic data buffer/controller of the present invention.

Also included in the improved ultrasonic inspection system shown in FIG. 1 is a FIG. 6 digital multi-channel ultrasonic data buffer/controller (UDBC) means 57 for generating 1K, 10K, 500K, 5M, 10M clock (CK) signals on respective lines 58a, 56b, 58c, 58d, 58e, one or more of which are used in devices 38, 37, 41, 51 and 57, and for generating the multiplexed transducer scanning signals on cable 33. UDBC means 57 is provided for processing plural sequences of corrected or uncorrected flaw echo pulses input on line 50 from ultrasonic instrument 36 and respective back echo pulses input on line 59 from device 45. UDBC means 57 processing is controlled by the internally generated transducer scanning signals on cable 33, externally generated maximum and minimum preset reference signals from respective devices 60, 61 fed over cable 62, 63, manual/auto load preset signals from device 64 fed over cable 65, and register preset signals fed from device 66 over cable 67. UDBC means 57 processing is also controlled by plate 10 position signal on line 68 and is synchronized with plate presence-absence signal on line 69, both from mill terminal 32. UDBC means 57 outputs an internally developed digital back echo signal on cable 70 to attenuation controller means 37 shown in FIG. 3 where it is used with the front echo signal to correct all echo pulse signals.

UDBC means 57 data processing function produces arrays of multi-level, priority-encoded, defect signals rippled to an output at cable 71 which interfaces with digital minicomputer 72 on a real-time high-speed basis, as hot plate 10 moves through inspection station 13. This feature permits digital minicomputer 72 to have a substantially reduced number of input/output operations and arithmetic calculations that would ordinarily be performed by minicomputer 72 in handling and analyzing ultrasonic test data. In this manner, UDBC means 57 aids minicomputer 72 in flaw area reconstruction relative plate 10 position while freeing same to perform other control and analysis tasks.

Also included in the improved ultrasonic inspection system shown in FIGS. 1 and 6 is digital processing means including the minicomputer 72 for flaw area analysis and reconstruction relative plate 10 position as described above, and a CRT/keyboard display terminal 73. Terminal 73 inserts plate 10 order data, other data, and other instructions, over two-way communication lines 74, 75 to minicomputer 72, and in turn through minicomputer 72 over lines 76, 77 to UDBC means 57, all as described below.

The aforesaid digital processing means minicomputer 72 is programmed to output on line 78 either of two types of encoded flaw area data and plate 10 temperature data fed over line 79 called by terminal 73 to digital printer 80. In turn, printer 80 produces either a printout as encoded flaw area map 81, shown in FIG. 7, or a printout as A.S.T.M. flaw evaluation 82, shown in FIG. 8. Both printouts relate to plate 10 defect position during passage through inspection station 13.

Turning now to FIG. 2, remote mill terminal 32 is provided with multi-channel pulser-delay/pulser-receiver 83 multiplexed over cable 84 by multi-channel mill remote control unit 85. Mill remote control unit 85 is controlled by the multi-channel transducer scanning signals on channel bus 33 from UDBC means 57, and interlocked with the presence of the plate position signal on line 29 and the plate presence-absence signal on line 31. Mill remote control unit 85 generates the multiplexed sequence on cable 84 to cause pulser-receiver device 83 to operate sequentially for each associated transducer in search unit 15.

Pulser-receiver device 83 is so circuited that when energized it transmits multi-channel R.F. pulses, one at a time, over cable 34 to a respective transducer in search unit 15 and causes the transducer to generate an ultrasonic beam which is passed through acoustical couplant 17 and into plate 10. Plate 10 experiences front, flaw and back echo beams received by the transducer in search unit 15 which cause the transducer energized to receive and generate corresponding sequence of front, flaw and back echo pulses until the next transducer channel is selected. Multi-channel receiver gain adjusters 86 are provided, one for each transducer channel, which act through cable 87 to equalize the R.F. echo pulse gain of each channel in pulser-receiver 83, regardless of variations in individual transducer channel characteristics. The multiplexing of pulser-receiver 83 causes remote mill terminal 32 to output one sequence of R.F. front, flaw and back echo pulses having an equalized preset gain for each channel on single channel output line 35. These sequences of echo pulses are subject to the aforesaid one or more transducer-detected sources of attenuation and/or timing errors.

Multi-channel mill remote control unit 85 in remote mill terminal 32 also transmits the plate position signal over line 68, and the plate presence-absence signal over line 69, both to the UDBC means 57 for use as described below.

Correction of each sequence of front, flaw and back echo pulses for one or more transducer-detected attenuation errors when present in signals on line 35 is processed in the first part of the cablibration means, namely, digital multi-channel automatic R.F. attenuation controller means 37, as shown on FIG. 3 and described below. Otherwise, when no attenuation errors are present, attenuation controller means 37 outputs uncorrected sequences of front, flaw and back echo pulses on line 40. Digital attenuation controller means 37 processes echo pulses having attenuation error relative a preset reference signal on cable 38, preset by device 39, by calculating and storing an attenuation correction factor. This correction factor is used to vary preset output gain proportional thereto, thus providing attenuation corrected sequences of front, flaw and back echo pulses on line 40.

The remaining portion of FIG. 2 shows a conventional modifiable main ultrasonic instrument means 37, such as a Branson Model 303, having a modified receive-only-but-not-transmit input and modified front, flaw and back echo gate outputs through which flow attenuation corrected or uncorrected sequences of respective echo pulses. In addition, a single clock source is replaced by multiple clock sources 1KCK, 10KCK, 500KCK, 5MCK and 10MCK on respective lines 58a, 58b, 58c, 58d, 58e, as well as the multiplexed transducer scanning signal source on channel bus 33, all output from UDBC means 57. If desired, all of the clock sources and channel bus source may alternatively be incorporated in new or existing main ultrasonic means 37.

Either attenuation corrected or uncorrected sequences of video front, flaw and back echo pulses on line 40 are applied at an input to single-channel R.F. amplifier 88, one channel sequence at a time, where the conventional pulse transmitter circuit is removed or disabled. The amount of amplification by amplifier 88 is preset by R.F. gain control 89. A fixed amount of attenuation of each sequence of video front, flaw and back echo pulses is set initially by DB attenuator 90, but varied thereafter only by corrective action as required by attenuation controller means 37. The attenuated sequence of video echo pulses is passed through tuned R.F. amplifier 91 which is characterized by frequency selector switch 92 and fed to one input of video amplifier 93 by way of filter selector 94 acting on a second input thereof.

A first output of video amplifier 93 feeds each sequence of attenuation corrected or uncorrected sequence of front, flaw and back echo pulses on line 95 to ultrasonic echo CRT display 51, clocked by 1KCK on line 58a, where the sequence is shown as trace 52. The particular transducer channel, or all channels of echo pulse trace 52 is determined by channel selector switch 53 signal on line 54 fed to CRT display 51 and attenuation controller means 37. A second output from video amplifier 93 is fed over line 96 to the inputs of respective front, flaw and back echo gates 97, 98, 99, each of which is clocked by 10KCK on line 58b. A third output from video amplifier 93 is fed to gate interface control 100 which outputs a basic echo pulse sequence timing signal to each of conventional modified front, flaw and back echo gate 97, 98, 99. The exact timing for echo pulse sequence for given plate 10 basic characteristics is preset by fine tuning respective delay adjusters 102, 103, 104. Gates 97, 98, 99 output front, flaw and back echo gate signals on lines 42, 50 and 43, resepectively, to video amplifier 93 to control the sequence of echo pulses illustrated by CRT trace 52.

Correction of each sequence of front, flaw and back echo pulses for one or more transducer-detected timing errors when present in signals on line 40 input to main ultrasonic instrument 36 is processed by the second part of the calibration means, namely, digital automatic flaw gate range controller 41 clocked by 10KCK, 10MCK, on lines 58b, 58e, and as shown in FIGS. 4 and 5 described below. Otherwise, when no timing errors are present, flaw gate range controller 41 causes respective gate 97, 98, 99 to output uncorrected sequences of front, flaw and back echo pulses on lines 42 50 and 53. Digital flaw range controller 41 receives flaw and back echo pulses having timing errors on lines 42, 43 and processes same relative preset signals on cable 44, derived from preset device 45, and initiated by a calibration start signal on liner 46 while being synchronized by the plate presence signal on line 31.

Controller means 41 processing function generates and stores a variable flaw gate off-time signal proportional to timing error detected between front and back echo pulses and output on line 47 along with back echo pulse on line 48 to device 45. Selection of manual-/automatic variable flaw gate off-time signal is made in device 45 and fed back to modify flaw echo gate 98 timing in main ultrasonic instrument 37, thereby outputting a timing-error corrected flaw echo pulse on line 50 to UDBC means 57. A slave back echo pulse is output from device 45 on line 59 and fed to the input of UDBC means 57 as described below.

FIG. 3 shows the digital multi-channel automatic R.F. attenuation controller means 37, combined with attenuation digital preset switch and display device 39, to form the first portion of the calibration means. Controller means 37 processes one or more transducer-detected attenuation errors when present in each sequence of echo pulses on line 35 so as to output each corrected or uncorrected sequence of front, flaw and back echo pulses on line 40. To accomplish digital processing of these signals within attenuation controller means 37, a number of preset and display signals are fed back and forth over cable 38 to preset switch and display device 39. Device 39 is provided with start pushbutton 105, minimum back echo reference preset switch 106 and zero attenuation preset switches 107, which output respective signals on line 108 and cables 109, 110, by way of cable 38 to attenuation controller means 37.

Within attenuation controller means 37 for correcting echo pulses with attenuation errors are conventional digital devices having, among others, control logic device 111 which is initiated by a start signal on line 108 and interacts with channel bus 33 digital signals to first achieve zero channel then others, the plate presence-absence signal on line 31 and clock pulses 10KCK and 500KCK on lines 58b and 58c. A digital comparator 112 is provided to compare the minimum back echo reference preset signal on data cable 109 with an actual digital back echo signal input on cable 70 for each of all channel sequences determined by channel bus 33. A single channel back echo difference data signal identified as a calculated correction factor for each echo pulse sequence is output on line 113 to control logic device 111.

Control logic device 111 produces four digital control signals in rapid sequence at the 10KCK clock rate and synchronized with the 500KCK clock signal in response to the channel bus 33 signals. A first control signal on line 114 at zero channel number first causes down counter 115 to be zeroed, then to preload a large number data equal to zero attenuation of plate 10 established by zero preset signal data on cable 110. A second control signal is first used internally to control the flow of the calculated correction factor data on line 113 over line 116 to "read data" input of first multi-channel random access memory (RAM) 117. A second function of the second control signal is output on line 118 to cause first RAM 117 to initially load to all digital ones during zero channel number, then be loaded with a zero at the one of the other multiplexed channel selected by channel bus 33 signals, if digital comparator 112 predetermined conditions are met. A third control signal on line 119 causes first RAM 117 low calculated correction factor data reading to be fed over line 120 to the "read data" input of second multi-channel RAM 121 each time that channel scan time occurs. A forth control signal on line 122 in conjunction with first RAM 117 output data on line 120 disables second RAM 121 from entering any new data, except during the second function of the second control signal on line 118 when all ones are in first RAM 117. This allows second RAM 121 to preload the maximum zero attenuation data from down counter 115.

Channel scan time is an interval that occurs at the 10KCK rate when zero channel number and higher numbers appear on channel bus 33 and endures as required for logic control device 111 to produce the aforesaid control signals and to further process each digital calculated correction factor data signal.

Logic control device 111 is so arranged that when plate presence signal is on line 31 and start signal is present on line 108, the control signals are produced and the data processing proceeds as follows. Before automatic attenuation gain control is run, the first scan cycle of the array of transducers in search unit 15 is used in the start-up to automatically zero each channel gain factor digital word transferred through multi-channel first RAM 117 and stored in second RAM 121. All channel zero gain values are stored in second RAM 121 so that the channel with the least gain displays a back echo pulse of at least 80% full screen trace on CRT display 51. All channel zero gain values stored as digital words in second RAM 121 are then reduced to meet reference count on cable 123 as compared to the maximum zero attenuation from down counter 115. Thus, at the end of the first scan cycle, all transducer channel echo signals operate from a uniform zero attenuation base even though actual zero may be slightly different for one or more transducers.

Automatic attenuation gain control is run after zeroing when the second and subsequent scanning cycles occur and as long as plate presence signal is on line 31. Control logic device 111 generates the above-described four digital control signals on lines 114, 118, 119, 122 for each scanning cycle. The zero-based calculated attenuation correction factor digital data words for each scanned channel stored in second RAM 121 are, at channel time, loaded one channel at a time over cable 124 into calculate latch 125.

Each channel calculated attenuation correction factor digital data is fed over cable 126 and converted into analog form in D/A device 127 which is stabilized by reference voltage source 128. The calculated attenuation correction factor output as analog current passes through optional fine adjust to R.F. attenuator 130. Device 130 varies output gain so that maximum input current causes zero attenuation, and a lesser value current a higher gain attenuation. Thus, multi-channel automatic attenuation controller means 37 varies R.F. echo pulse sequence for every transducer, one channel at a time, to correct for one or more transducer-detected echo pulse attenuation errors when they occur. The automatic attenuation gain control will run each scanning cycle until the trailing end of plate 10 causes a plate absence signal on line 31, thus causing the stoppage of digital data processing in digital logic device 111.

Attenuation controller means 37 includes two additional features. First, the particular calculated attenuation correction factor digital data in calculate latch 125 is also fed over cable 131 to display latch 132 which holds such data for any given transducer channel determined by a channel selection on line 55 from a first stage of channel selector switch 53. This data is stored in programmable read only memory (PROM) 133. In turn, device 133 energizes driver 134 and outputs over cable 135 (part of larger cable 38) the specific percentage attenuation correction factor on display device 136, incorporated in device 39, of which R.F. attenuator 130 varied output gain for that channel.

The second and last feature of attenuation controller means 37 is the display of the particular channel number associated with the attenuation correction factor on digital display 136. The particular channel number is determined by a second stage of channel selector switch 53, encoded in encoder 137, fed to PROM 138, then to driver 139. Driver 139 outputs over cable 140 (part of larger cable 38) the specific preselected channel number on digital display device 141, which is also incorporated in device 39.

Reference will now be made to FIGS. 4 and 5 where the automatic flaw gate range controller means 41 performs the second portion of the calibration means for correcting one or more transducer-detected timing errors, namely, echo pulse timing errors. FIG. 4 illustrates plate 10 thickness variations in a range of ordered sizes between $T_1$ and $T_2$ relative a fixed front surface adjacent search unit 15 and a variable distant back surface. Plate 10 rolling tolerances may also cause a $T_1$ thickness variation for a given plate anywhere between its edges and ends. Thus, all thickness variations cause corresponding timing errors in flaw and back echo pulses compared to the initial thickness setting done manually in main ultrasonic instrument 36. In addition, transducer gap variation between the front surface of plate 10 and search unit 15, sometimes caused by plate waviness, also cause corresponding timing errors in flaw and back echo pulses.

Generally, plate 10 moves at too rapid a line speed past search unit 15 for on-line manual adjustments to be made in main ultrasonic instrument 36 to correct for echo pulse timing errors caused by either plate thickness or transducer gap variations. When determining internal quality of a variety of products there are a number of echo pulses caused by each transducer, one each front, flaw and back echo pulse sequence caused by said transducer is of interest to an inspector. Manual operation and echo pulse signal interpretation usually requires an operator to view the display screen of CRT 51 shown in FIG. 2. The operator must observe all signals on the display screen and interpret only those signals known through experience to be relevant to the ultrasonic inspection method.

For these reasons, digital automatic flaw gate range controller means 41, including preset device 45, shown in FIG. 5, is provided to operate with modified gate circuits in main ultrasonic instrument 36 for on-line automatic analysis of each transducer sequence of echo pulses and adjustment of flaw echo gate 98 timing during a scan cycle to eliminate manual adjustments. Relevant front, flaw and back echo pulses are separated from unwanted multiples thereof by conventionally adjusting corresponding delays for gate in main ultrasonic instrument 36 as described above for a predetermined plate 10 thickness.

It should be remembered that there are always front and back echo pulses and that front echo gate 97 is "on" only during the time it takes front echo pulse to transverse fluid couplant 17 and a finite thickness of plate 10 front surface. Further, that flaw gate 98 turns "on" an instant after front echo gate 97 turns "off", and an instant before back echo gate 99 turns "on" flaw echo gate 98 turns "off". This references the back echo gate 99 operation to the flaw gate 98 "off" time. Moreover, when plates 10 of differing thickness $T_1$ or $T_2$ are inspected, flaw echo gate 98 starting point or turn "on" time remains unchanged, but the stopping or turn "off" time point must be increased or decreased to occur just before the variable position of the back echo pulse. This change in flaw echo gate 98 timing to accommodate various plate 10 thicknesses is done automatically by generating a corresponding variable flaw echo gate "off" time signal in digital controller means 41 and outputting same on line 47, and subsequently in a feedback loop on line 49, to modify flaw echo gate 98 "off" time proportional thereto.

Turning now to FIG. 5, there is shown the digital automatic flaw gate range controller means 41 which, together with flaw gate start and digital preset switch device 45, produce the variable flaw gate "off" time signal on line 47. Control logic device 142 receives channel bus 33, video flaw and back echo gate signals on respective lines 42,43, includes flaw and back echo amplitude sensing circuits, and is synchronized by clock signals 10KCK and makes use of high-speed clock signals 10MCK from respective lines 58c, 58e. When there is a plate presence signal on line 31 and when initiated by a gate calibrate start signal on line 46 from gate calibrate pushbutton 143, control logic device 142 controls the flow of flaw and back echo gated pulses to a series of counters which eventually develop the variable flaw gate "off" time signal. Echo pulse flow to these counters occur at a 10MCK clock rate so that a precise "off" time determination may be made during each channel scan time of echo pulse sequences and that a change, when necessary, may be made at the end of transducer scanning cycle.

When gate calibrate start signal and plate presence signal on respective lines 46, 30 are received, control logic device 142 starts flaw echo gate 98 "on" time and increments from zero count calibration counter 144 via line 145 and flaw gate range counter 146 via line 147. If no flaw echo pulse is present in flaw echo gate 98, both counters 144, 146 continue to count up to overflow. An overflow on calibration counter 144 reinitiates the calibration start sequences. However, if the back echo pulse is present during flaw echo gate 98 "on" time, the calibration counter 144 is stopped, but the flaw gate range counter 146 continues to count until it overflows, then is stopped. At this occurrence, calibration counter 144 contains a digital value representing flaw echo gate 98 range and the flaw gate range counter 146 has a value of zero.

A third counter, decrement counter 148 receives a digital equivalent of zero thickness signal on cable 149, part of larger cable 44, from zero thickness preset switches 150 included in device 45. The value of decrement counter 148 is output on line 153 and used to decrement calibration counter 144 a small amount until the back echo pulse no longer is present in flaw echo gate "on" time. This continues during each channel scan time of normal plate inspection procedures and when stopped calibration counter 144 digital value is output on cable 154.

Calibration counter 144 output on cable 154 is fed to complementing multiplexers 155 which also receives a manual preset thickness signal over cable 156, also part of larger cable 44, from manual thickness setting switches 157 included in device 45. Prior to the start of the next channel scan time, the digital complement of the final value in calibration counter 144 is fed over cable 158 and loaded into flaw gate range counter 146. Thus, on the next scanning cycle, flaw gate range counter 146 starts counting from the complement of the value which represents flaw echo gate 98 range of "on" time. When overflow is reached, flaw echo gate range counter 146 outputs a flaw echo gate turn "off" signal on line 47. The value in flaw echo gate range counter 146 remains until reset by a signal on line 147 when either the end of plate 10 is detected by the loss of plate signal on line 31 and a new plate 10 generates another plate presence signal on line 31, or by closing calibration start pushbutton 143 any time.

The flaw echo gate turn "off" signal from flaw echo gate range counter 146 varies automatically proportional to plate thickness $T_1$ to $T_2$ and is output on line 47 to manual/automatic selector switch 159. In addition, an unmodified flaw echo gated signal on line 160, along with the back echo gated signal on line 48, is fed from control logic device 142 to manual/automatic selector switch 159.

Selector switch 159 determines the calibration mode of flaw echo gate turn "off" signal fed back in a loop on line 49 to flaw echo gate 98 in modified main ultrasonic instrument 37. In manual position, switch 159 connects uncorrected flaw echo signals from line 160 directly to the feedback loop on line 49. In the automatic position, switch 159 connects corrected flaw echo signals from line 47 to be output on feedback loop line 49 which have been corrected for timing errors due to plate 10 thickness or transducer gap variations. In this manner, modified gain ultrasonic instrument 37 will output either uncorrected or corrected flaw echo pulses on line 50 to the ultrasonic data buffer/controller (UBDC) 57 for digital signal processing as described below. Selector switch 159 also outputs a valve back echo gated signal on line 59 to UDBC 57 in both manual and automatic mode positions.

The ultrasonic data buffer/controller (UDBC) 57 for generating clock signals and processing, encoding and storing corrected or uncorrected flaw echo signals and aiding in flaw area reconstruction with minicomputer 72 is shown in FIG. 6. UDBC 57 includes master channel scan clocks 161 which produces a plurality of synchronized clock signals. First, a channel bus source of binary multiplex channel selection signals at 10KCK on cable 33 used internally and externally as noted above. Five additional clock sources are included, namely, 1KCK, 10KCK, 500KCK, 5MCK and 10MCK clock sources which are output from device 161 on respective lines 58a, 58b, 58c, 58d and 58e for use internally and externally as described above.

Another feature of UDBC 57 is its high-speed, on-line digital processing capabilities which peak detects and converts conventional ultrasonic analog signals of, for example, either corrected or uncorrected flaw echo gate pulse origin on line 50, as well as back echo gated pulse origin on line 59, into digital forms by means of respective flaw echo pulse A/D 162 and back echo pulse A/D 163. Both devices 162, 163 are initiated at the 10KCK rate input thereto on line 58b. A positive, or negative, digital peak amplitude of the corrected or uncorrected flaw echo gated pulse is output from device 162 on cable 164 to digital divider 165. Device 165 is clocked by the 5MCK source on line 58d. A positive, or negative, digital peak amplitude of the back echo gated pulse is output from device 163 on cable 70 to both digital divider 165 and device 112 in multi-channel automatic R.F. attenuation controller for use as described above.

Digital divider 165 then divides the digital peak flaw echo signal on cable 164 by the digital peak back echo signal on cable 70 to establish a digital ratio of these two signals on cable 166. The digital ratio is compared to large and small defect digital references presettable in respective maximum digital comparator 167 and minimum digital comparator 168. An actual digital maximum reference signal is preset and input to device 167 on cable 169 by maximum preset switches and display device 60. Device 60 includes a digital display of the maximum flaw reference value fed thereto over cable 170 from device 167. Cables 169, 170 are part of larger cable 62. An actual digital minimum reference signal is preset and input to device 168 on cable 171 by minimum preset switches and display device 61. Device 61 includes a digital display of the minimum flaw reference value fed thereto over cable 172 from device 168. Cables 171, 172 are part of larger cable 63.

Output from comparator devices 167, 168 are digital maximum and minimum flaw referenced values on respective lines 174, 175, which are input to priority encoder 176. Priority encoder 176 produces a digital flaw value for the transducer scanned by search unit 15 as an output on cable 177 according to a predetermined flaw priority level established for the input signals. Actually, any order of priority may be assigned to the input signals. This choice is exemplified in UDBC 57 as four decimal flaw priority levels in two-bit binary code form on cable 177 and tabulated in "FLAW PRIORITY LEGEND" on the lower left-hand corner of FIG. 6. Level "0" is designated a valid inspection of one incremental area of plate 10 inspected by one transducer in search unit 15 because a back echo was present without a flaw echo. Level "1" is designated a questionable inspection of the incremental area because insufficient amplitude of both back and flaw echoes were present. Level "2" is designated a small flaw and level "3" is designated as a large flaw, both because of their numerical ratio value of the flaw to back echo pulses. By additional flaw level encoding in device 176, different degrees of flaw resolution of plate 10 may be had, if desired.

The two-bit binary code flaw level output on cable 177 is temporarily stored for one or more complete transducer scan cycles of search unit 15 in multi-channel data register 178 under control of the scanning signals on channel bus 33. More than one scan cycle will enhance the reliability of the flaw data encoding. Any one or no channel may be selected for subsequent processing by multi-channel register preset switch 66 feeding such selection over cable 67 to register 178. Data processing is carried out by preset switch 66 substituting multi-channel flaw level test data in register 178 for actual data from encoder 176. The two-bit per channel flaw level data, regardless of whether actual or test data, is output on cable 179 and finally stored as parallel data in high-speed first-in first-out (FIFO) memory stacks 180. This parallel data is stored in FIFO memory 180 for a plurality of scan cycles having an address associated with plate 10 position during inspection. This corrected or uncorrected flaw level data is output on cable 181, via drivers 182 and cable 71, for computer 72 analysis under control of plate 10 position information as will be described below. It should be remembered that the presetting functions of multi-channel register preset switches 66 not only tests the function of register 178, but those of FIFO memory 180, drivers 182 and a corresponding portion of computer 72.

A digital interface control and simulator 182, which is clocked by the 500KCK signal on line 58c, receives manual load simulated flaw signals on line 184 from manual/automatic load switches 64. An indication of such load simulation is fed over cable 185 to displays in device 64, the cables 184, 185 being part of larger cable 65. Simulator 183 is interlocked via line 186 with master channel scan clocks 161. When switches are in manual mode, a flaw simulation signal is fed from simulator 183 over line 187 to FIFO memory 180 to simulate any one of the aforesaid four flaw levels in FIFO memory 180. When switches 64 are in automatic mode, no simulation signal is on line 187 and FIFO memory 180 performs as described above.

Multi-Channel data register 178, which normally feeds FIFO memory 180, is synchronized not only with channel scan signal source on channel bus 33 but with forward/reverse line counter register 188. Device 188, which itself is synchronized with the 5MCK and 10MCK clock sources on lines 58d, 58e, respectively, receives the forward/reverse plate position signal on line 68, from say a roto-pulser device, and the plate presence signal on line 69. Device 188 outputs one line 189 a forward coded pulse corresponding to plate 10 travel in forward direction along inspection path 11 at the end of each search unit 15 scan. In this manner, the forward coded pulse acting on multi-channel data register 178 causes same to dump parallel encoded flaw data into FIFO memory 180 and ripple therethrough sequentially on plate 10 forward travel. Conversely, when plate 10 travels in the reverse direction through the lines of lateral incremental test areas, device 188 outputs on line 189 a reverse coded pulse which acts on device 178 to inhibit flow of flaw data into FIFO memory 180, and causes memory 180 to hold the last plate 10 forward travel flaw data until forward plate travel is signalled on line 189.

Up-/down-counting line coded pulses corresponding to plate 10 forward/reverse position produced by line counter register 188 is output on line 190 to computer 72. Computer 72 is arranged to perform two functions in response to these coded pulses on line 190 and a plate presence/absence signal on line 191 also from device 188. First, computer 72 stores the last up-count line pulses at the end of plate 10 forward travel and allows FIFO memory 180 to ripple the four-level encoded flaw data to computer 72 in a normal manner. Second, when the last up-count is stored, computer 72 sends a disabling signal over line 77 which dumps the FIFO memory 180 flaw data.

During plate 10 reverse travel, the down-counting of coded line pulses is compared to the last up-count line stored value. When plate 10 direction is returned to forward travel and the up-count line pulses equal the stored value thereof, computer 72 sends an enabling signal over line 77 to allow FIFO memory 180 to output normally and ripple four-level encoded flaw data therethrough. When plate 10 absence is detected, a signal on line 191 causes computer 72 to send a parallel dump signal over line 77 to dump the data from FIFO memory 180.

CRT/keyboard display terminal 73 is arranged to cause computer 72 to communicate a request over line 77 to FIFO memory 180 to also unload the four-level priority encoded flaw data into computer 72.

Thus, it will now be appreciated that the UDBC 57 shown in FIG. 6 performs high-speed, on-line, digital flaw data processing in hardware form what are normally time consuming operations in a computer. For example, the entire operating time of UDBC 57 is about the same as a division operation alone in the computer. In this connection, computer 72 may be a time-sharing manufacturing process control minicomputer to perform slower but more extensive and important arithmetic operations, or may be a dedicated microcomputer, if desired. UDBC 57 permits computer 72 to operate asynchronously with the ultrasonic plate inspection system operations. This frees computer 72 for data analysis, an operation to which it is better suited.

Computer 72 is programmed to receive corrected or uncorrected multi-level, priority-encoded, flaw data over cable 71, plate 10 temperature data on line 79 taken at the ultrasonic inspection station 13, plate order data and other heading data from CRT/keyboard display terminal 73, and plate 10 position signals on line 190. Computer 72 analyzes these data and reconstructs and stores on a real time basis flaw area data as plate 10 travels through inspection station 13. Digital flaw plotter 80 outputs hard copy of either, or both, flaw map 81, shown in FIG. 7 or A.S.T.M. flaw evaluation 82, shown in FIG. 8.

FIG. 8 A.S.T.M. flaw evaluation illustrates the computer-based analysis of another plate, this time using A.S.T.M. A-578 specification for the full number of transducer channels in search unit 15 over 1093 scan cycles related to plate position in the reconstruction of the flaw evaluation. In this illustration, all scanning channels having either flawed or clear areas are shown bracketed in the interest of conserving hard copy. Header data are included in FIG. 8 which are similar to those described above for FIG. 7.

Returning now to FIGS. 1, 2, 3, 5 and 6, the automatic on-line inspection system having self-diagnostic features referred to above which are readily maintainable by mill operating personnel will now be described. These self-diagnostic features relate to testing of equipment or circuit operations of the acoustical couplant source 16, attenuation and timing error correction of echo pulses by calibration means 37, 41 and computer-aided flaw area reconstruction by high-speed ultrasonic data buffer/controller means (UDBC) 57 which frees computer 72 for other laborious process calculations.

Referring to FIGS. 1 and 2, improper operation or the effectiveness of ultrasound acoustical couplant 17 between plate 10 and search unit 15 may be self-diagnosed through simulation. This is done by varying the preset plate temperature relationship to fluid couplant 17, a known amount using ultrasound fluid couplant supply valve 20 to control the flow of said fluid. All other portions of the inspection system operating properly, there should be a noticeable change in amplitude of echo pulse trace 52 appearing in CRT display 51. If not, the adjustable ultrasound fluid couplant portion of the system should be serviced.

Using FIGS. 2 and 3, improper operation of multi-channel R.F. attenuation controller means 37 for correcting front flaw and back echo pulses for one or more transducer-detected attenuation errors due to variations in plate 10 temperature and/or alloy or composition may be self-diagnosed through simulation. Referring to attenuation digital preset switches and displays 39, by adjusting either minimum back echo reference and/or zero attenuation preset switches 106, 107 to another digital value from that used during normal operation, and after closing start pushbutton 105, the attenuation condition of any or all circuits of transducer channel(s) determined by channel selector switch 53, as well as the calculated correction factor will be determined and presented on attenuation factor display 136 and channel number display 141. In addition, the newly calculated correction factor will cause R.F. attenuator 130 to vary output gain accordingly on line 40 and cause a corresponding change in amplitude in echo pulse trace 52 on CRT display device. Otherwise, either one or more transducer cables or circuit components affecting plate property test simulations and correction may have become defective and should be serviced.

Referring to FIGS. 2 and 5, improper operation of automatic flaw gate range controller means 41 for correcting flaw echo pulses for transducer-detected timing errors due to variations in plate 10 thickness and/or transducer gap may be self-diagnosed through simulation. Referring to flaw gate start and digital reference preset switches 45, by adjusting zero preset switch 150 and/or manual thickness setting switches 157 to different values than normally preset, and by pressing gate calibrate push-button 143, a newly calculated flaw echo gate turn "off" signal will be output on line 49 when switch 159 is in automatic mode, thereby causing a corresponding change in correction of flaw echo timing in trace 52 on CRT tube 51. By changing switch 159 to manual mode of operation, no correction of flaw echo pulse timing will take place and no change in flaw echo pulse timing should take place in trace 52 of CRT display 51. Otherwise, circuit components affecting plate 10 thickness and/or transducer gap test simulation and correction may have become defective and should be serviced.

Using FIG. 6, improper operation of ultrasonic data buffer controller means 57 for high-speed generating of plural clock pulses, prioritizing and storing corrected or uncorrected flaw data for computer-based flaw area reconstruction may be self-diagnosed through simulation. Referring to maximum and minimum reference preset switches 60, 61, respectively, by varying either or both said switches from original settings a new ratio of defect severity will be encoded by device 176, and depending upon which transducer channel is pre-selected by switch device 66, then FIFO memory 180 will store a different flaw value for computer 72, which value may be observed on CRT/keyboard display terminal 73. In addition, load switches 64, when in manual mode, will cause a simulation of priority-encoded flaws which will also cause FIFO memory 180 to display the simulated value on display terminal 73 for every transducer channel selected by switch device 66. When in automatic mode, load switches 64 do not cause any simulation action. Otherwise, circuit components affecting flaw level simulation and priority-encoding in flaw area reconstruction for use with computer 72 may have become defective and should be replaced.

Finally, any of the presetting and display and/or simulation features of hard-wired devices, such as temperature controller 23, attenuation digital preset switch and display device 39, flaw gate start and digital reference preset switches 45, and devices 60, 61, 64, 66 associated with UDBC means 57, may be included in the program used with computer 72. In this manner, all preset and simulation functions will be carried out by mill operating personnel communicating through the keyboard on terminal 73 to computer 72 and observing same on the CRT display of terminal 73 under an additional subroutine used for flaw area data analysis.

We claim:

1. In an ultrasonic inspection system for determining area defects in a flat workpiece movable along an inspection path and which is subject to one or more error-causing variable test conditions, said system including multi-channel ultrasonic pulse-echo tester means and calibration means for correcting a transducer-detected echo-pulse error, both responsive to a multiplexed array of transducers signaled by transducer scanning signals, said tester means having an ultrasonic instrument outputting plural sequences of front echo, flaw echo and back echo gated pulses per sequence derived from multiplexed testing of lateral incremental areas of the workpiece, there also being means for producing a position signal representing workpiece location at each lateral incremental area tested along the inspection path, as well as multi-channel ultrasonic data buffer/controller means for generating clock signals and the scanning signals and for processing arrays of multi-channel lateral area flaw echo pulses and respective back echo pulses under control of the scanning signals and the workpiece position signal, said calibration means including:

(a) digital multi-channel automatic attenuation controller means acting in response to the multiplexed sequence of said echo pulses and a preset reference signal for correcting each echo pulse attenuation error, said controller means varying preset output gain proportional to attenuation error caused by each test transducer detecting one or more test condition variables including workpiece alloy or composition and temperature, said controller means outputting to a modified input of the ultrasonic instrument attenuation-error corrected front, flaw and back echo pulses, the corrected flaw and back echo pulses also used in the multi-channel ultrasonic data buffer/controller means; and said pulse-echo tester means includes:

(a) a search unit having a multi-channel array of ultrasonic transducers, each transducer acoustically coupled to a different lateral incremental area of the workpiece;

(b) an adjustable supply and return sources of ultrasound fluid for providing the transducer acoustical coupling and a coolant to a hot workpiece; and (c) workpiece temperature sensor and indicator means for adjusting the fluid supply to a known value related to workpiece cooling and effect of temperature on acoustical coupling.

2. In an ultrasonic inspection system for determining defects in a flat workpiece movable along an inspection path and which is subject to one or more error-causing variable test conditions, said system including multi-channel ultrasonic pulse-echo tester means and calibration means for correcting a transducer-detected echo-pulse error, both responsive to a multiplexed array of transducers signaled by transducer scanning signals, said tester means having an ultrasonic instrument outputting plural sequences of front echo, flaw echo and back echo gated pulses per sequence derived from multiplexed testing of lateral incremental areas of the workpiece, there also being means for producing a position signal representing workpiece location at each lateral incremental area tested along the inspection path, as well as multi-channel ultrasonic data buffer/controller means for generating clock signals and the scanning signals and for processing arrays of multi-channel lateral area flaw echo pulses and respective back echo pulses under control of the scanning signals and the workpiece position signal, said calibration means including:

(a) digital automatic flaw gate range controller means acting in response to the multiplexed sequence of said echo pulses and a preset reference signal for correcting each flaw echo pulse timing error, said controller means varying preset flaw gate off-time in a feedback loop to a modified ultrasonic instrument proportional to timing error caused by each test transducer detecting one or more test condition variables including workpiece thickness and transducer gap, said controller means causing the ultrasonic instrument to output a timing-error corrected flaw echo pulse to the multi-channel ultrasonic data buffer/controller means; and said pulse-echo tester means includes:

(a) a search unit having a multi-channel array of ultrasonic transducers, each transducer acoustically coupled to a different lateral incremental area of the workpiece;

(b) an adjustable supply and return sources of ultrasound fluid for providing the transducer acoustical coupling and a coolant to a hot workpiece; and (c) workpiece temperature sensor and indicator means for adjusting the fluid supply to a known value related to workpiece cooling and effect of temperature on acoustical coupling.

3. In an ultrasonic inspection system for determining area defects in a flat workpiece movable along an inspection path and which may be subject to one or more error-causing variable test conditions, said system including multi-channel ultrasonic pulse-echo tester means, and when desired, multi-channel calibration means for correcting a transducer-detected error, both means responsive to a multiplexed array of transducers signaled by transducer scanning signals, said tester means outputting plural sequences of front echo, flaw echo and back echo gated pulses per sequence derived from multiplexed testing of lateral incremental areas of the workpiece, each said echo pulse susceptible of one or more test error corrections, there also being means for producing a position signal representing workpiece location at each lateral incremental area tested along the inspection path, said system further including:

(a) digital multi-channel ultrasonic data buffer/controller means interconnectable with said ultrasonic instrument for generating clock signals and the multiplexed transducer scanning signals, and for processing plural sequences of corrected or uncorrected flaw echo pulses and respective back echo pulses under control of the transducer scanning signals, a preset reference signal, and the workpiece position signal, thereby to produce arrays of multi-level, priority-encoded, defect signals rippled to an output which will aid a computer in workpiece flaw area reconstruction; and (b) said pulse-echo tester means including:
  1. a search unit having a mult-channel array of ultrasonic transducers, each transducer acoustically coupled to a different lateral incremental area of the workpiece;
  2. an adjustable supply and return sources of ultrasound fluid for providing the transducer acoustical coupling and a coolant to a hot workpiece; and
  3. workpiece temperature sensor and indicator means for adjusting the fluid supply to a known value related to workpiece cooling and effect of temperature on acoustical coupling.

4. An ultrasonic inspection system for determining area defects in a flat workpiece movable along an inspection path and which may be subject to one or more error-causing variations in test conditions including workpiece alloy or composition, temperature, thickness and transducer gap, said system comprising:
 (a) pulse-echo tester means producing a source of multi-channel ultrasonic echo pulses having a preset gain and output in corresponding sequences of front echo, flaw echo and back echo pulses per sequence from an array of transducers, said echo pulses derived from multiplexed transducer scanning signals causing testing of lateral incremental areas of the workpiece, each said echo pulse susceptible to one or more test error corrections;
 (b) modifiable ultrasonic instrument means producing a single-channel sequence of front echo, flaw echo and back echo gates and outputting corresponding front echo, flaw echo and back echo gated pulses per sequence, said output derived from multiplexing each multi-channel testing of lateral incremental areas of the workpiece in response to the scanning signals;
 (c) when desired, calibration means including controller means acting on a modified ultrasonic instrument and in response to a multiplexed sequence of said echo pulses and a preset reference signal for correcting echo pulse error proportional to one or more of said transducer-detected test condition variables causing said error;
 (d) means for producing a position signal representing workpiece location at each lateral incremental area tested along the inspection path; and
 (e) multi-channel ultrasonic data buffer/controller means interconnectable with said ultrasonic instrument for generating clock signals and the multiplexed transducer scanning signals, and for processing plural sequences of corrected or uncorrected flaw echo pulses and respective back echo pulses under control of the multiplexed transducer scanning signals and the workpiece position signal, thereby to produce arrays of multi-level, priority-encoded, defect signals rippled to an output which will aid a computer in workpiece flaw area reconstruction; and
 (f) said pulse-echo tester means including:
  1. a search unit having a multi-channel array of ultrasonic transducers, each transducer acoustically coupled to a different lateral incremental area of the workpiece;
  2. an adjustable supply and return sources of ultrasound fluid for providing the transducer acoustical coupling and a coolant to a hot workpiece; and
  3. workpiece temperature sensor and indicator means for adjusting the fluid supply to a known value related to workpiece cooling and effect of temperature on acoustical coupling.

5. An ultrasonic inspection system for determining area defects in a flat workpiece movable along an inspection path and which may be subject to one or more error-causing variations in test conditions including workpiece alloy or composition, temperature, thickness and transducer gap, said system comprising:
 (a) pulse-echo tester means producing a source of multi-channel ultrasonic echo pulses having a preset gain and output in corresponding sequences of front echo, flaw echo and back echo pulses per sequence from an array of transducers, said echo pulses derived from multiplexed transducer scanning signals causing testing of lateral incremental areas of the workpiece, each said echo pulse susceptible to one or more test error corrections;
 (b) modifiable ultrasonic instrument means producing a single-channel sequence of front echo, flaw echo and back echo gates and outputting corresponding front echo, flaw echo and back echo gated pulses per sequence, said output derived from multiplexing each multi-channel testing of lateral incremental areas of the workpiece in response to the scanning signals;
 (c) when desired, calibration means including controller means acting on a modified ultrasonic instrument and in response to a multiplexed sequence of said echo pulses and a preset reference signal for correcting echo pulse error proportional to one or more of said transducer-detected test condition variables causing said error;
 (d) means for producing a position signal representing workpiece location at each lateral incremental area tested along the inspection path;
 (e) multi-channel ultrasonic data buffer/controller means interconnectable with said ultrasonic instrument for generating clock signals and the multiplexed transducer scanning signals, and for processing plural sequences of corrected or uncorrected flaw echo pulses and respective back echo pulses under control of the multiplexed transducer scanning signals and the workpiece position signal, thereby to produce arrays of multi-level, priority-encoded, defect signals rippled to an output; and
 (f) digital processing means including a computer and terminal interactable with the multi-channel ultrasonic data buffer/controller, the multi-channel, multi-level, priority-encoded defect output signals, and the workpiece position signal for workpiece flaw area reconstruction, and if desired, further including means for producing one or more types of printouts of an encoded flaw area map and an encoded flaw area evaluation relative test position of the workpiece; and
 (g) said pulse-echo tester means including:
  1. a search unit having a multi-channel array of ultrasonic transducers, each transducer acoustically coupled to a different lateral incremental area of the workpiece; and
  2. an adjustable supply and return sources of ultrasound fluid for providing the transducer acoustical coupling and a coolant to a hot workpiece; and
  3. workpiece temperature sensor and indicator means for adjusting the fluid supply to a known value related to workpiece cooling and effect of temperature on acoustical coupling.

6. In an ultrasonic inspection system for determining area defects in a flat workpiece movable along an inspection path and which is subject to one or more error-causing variable test conditions, said system including multi-channel ultrasonic pulse-echo tester means and calibration means for correcting a transducer-detected echo-pulse error, both responsive to a multiplexed array of transducers signaled by transducer scanning signals, said tester means having an ultrasonic instrument outputting plural sequences of front echo, flaw echo and back echo gated pulses per sequence derived from multiplexed testing of lateral incremental areas of the workpiece, there also being means for producing a position signal representing workpiece location at each lateral incremental area tested along the inspection path, as well as multi-channel ultrasonic data buffer/controller means for generating clock signals and the scanning signals and for processing arrays of multi-channel lateral area flaw echo pulses and respective back echo pulses under control of the scanning signals and the workpiece position signal, said calibration means including:

(a) digital multi-channel automatic attenuation controller means acting in response to the multiplexed sequence of said echo pulses and a preset reference signal for correcting each echo pulse attenuation error, said controller means varying preset output gain proportional to attenuation error caused by each test transducer detecting one or more test condition variables including workpiece alloy or composition and temperature, said controller means outputting to a modified input of the ultrasonic instrument attenuation-error corrected front, flaw and back echo pulses, the corrected flaw and back echo pulses also used in the multi-channel ultrasonic data buffer/controller means; and said pulse-echo tester means includes:

(a) a search unit having a multi-channel array of ultrasonic transducers, each transducer acoustically coupled to a different lateral incremental area of the workpiece;

(b) an adjustable supply and return sources of ultrasound fluid for providing the transducer acoustical coupling and a coolant to a hot workpiece; and (c) workpiece temperature sensor and controller means for automatically adjusting the fluid supply to maintain a known value related to workpiece cooling and effect of temperature on acoustical coupling.

7. In an ultrasonic inspection system for determining defects in a flat workpiece movable along an inspection path and which is subject to one or more error-causing variable test conditions, said system including multi-channel ultrasonic pulse-echo tester means and calibration means for correcting a transducer-detected echo-pulse error, both responsive to a multiplexed array of transducers signaled by transducer scanning signals, said tester means having an ultrasonic instrument outputting plural sequences of front echo, flaw echo and back echo gated pulses per sequence derived from multiplexed testing of lateral incremental areas of the workpiece, there also being means for producing a position signal representing workpiece location at each lateral incremental area tested along the inspection path, as well as multi-channel ultrasonic data buffer/controller means for generating clock signals and the scanning signals and for processing arrays of multi-channel lateral area flaw echo pulses and respective back echo pulses under control of the scanning signals and the workpiece position signal, said calibration means including:

(a) digital automatic flaw gate range controller means acting in response to the multiplexed sequence of said echo pulses and a preset reference signal for correcting each flaw echo pulse timing error, said controller means varying preset flaw gate off-time in a feedback loop to a modified ultrasonic instrument proportional to timing error caused by each test transducer detecting one or more test condition variables including workpiece thickness and transducer gap, said controller means causing the ultrasonic instrument to output a timing-error corrected flaw echo pulse to the multi-channel ultrasonic data buffer/controller means; and said pulse-echo tester means includes:

(a) a search unit having a multi-channel array of ultrasonic transducers, each transducer acoustically coupled to a different lateral incremental area of the workpiece;

(b) an adjustable supply and return sources of ultrasound fluid for providing the transducer acoustical coupling and a coolant to a hot workpiece; and (c) workpiece temperature sensor and controller means for automatically adjusting the fluid supply to maintain a known value related to workpiece cooling and effect of temperature on acoustical coupling.

8. In an ultrasonic inspection system for determining area defects in a flat workpiece movable along an inspection path and which may be subject to one or more error-causing variable test conditions, said system including multi-channel ultrasonic pulse-echo tester means, and when desired, multi-channel calibration means for correcting a transducer-detected error, both means responsive to a multiplexed array of transducers signaled by transducer scanning signals, said tester means outputting plural sequences of front echo, flaw echo and back echo gated pulses per sequence derived from multiplexed testing of lateral incremental areas of the workpiece, each said echo pulse susceptible of one or more test error corrections, there also being means for producing a position signal representing workpiece location at each lateral incremental area tested along the inspection path, said system further including:

(a) digital multi-channel ultrasonic data buffer/controller means interconnectable with said ultrasonic instrument for generating clock signals and the multiplexed transducer scanning signals, and for processing plural sequences of corrected or uncorrected flaw echo pulses and respective back echo pulses under control of the transducer scanning signals, a preset reference signal, and the workpiece position signal, thereby to produce arrays of multi-level, priority-encoded, defect signals rippled to an output which will aid a computer in workpiece flaw area reconstruction; and (b) said pulse-echo tester means including:

1. a search unit having a multi-channel array of ultrasonic transducers, each transducer acoustically coupled to a different lateral incremental area of the workpiece;

2. an adjustable supply and return sources of ultrasound fluid for providing the transducer acoustical coupling and a coolant to a hot workpiece; and 3. workpiece temperature sensor and controller means for automatically adjusting the fluid supply to maintain a known value related to workpiece cooling and effect of temperature on acoustical coupling.

9. An ultrasonic inspection system for determining area defects in a flat workpiece movable along an inspection path and which may be subject to one or more error-causing variations in test conditions including workpiece alloy or composition, temperature, thickness and transducer gap, said system comprising:

(a) pulse-echo tester means producing a source of multichannel ultrasonic echo pulses having a preset gain and output in corresponding sequences of front echo, flaw echo and back echo pulses per sequence from an array of transducers said echo pulses derived from multiplexed transducer scanning signals causing testing of lateral incremental areas of the workpiece, each said echo pulse susceptible to one or more test error corrections;

(b) modifiable ultrasonic instrument means producing a single-channel sequence of front echo, flaw echo and back echo gates and outputting corresponding front echo, flaw echo and back echo gated pulses per sequence, said output derived from multiplexing each multichannel testing of lateral incremental areas of the workpiece in response to the scanning signals;

(c) when desired, calibration means including controller means acting on a modified ultrasonic instrument and in response to a multiplexed sequence of said echo pulses and a preset reference signal for correcting echo pulse error proportional to one of more of said transducer-detected test condition variables causing said error;

(d) means for producing a position signal representing workpiece location at each lateral incremental area tested along the inspection path; and (e) multi-channel ultrasonic data buffer/controller means interconnectable with said ultrasonic instrument for generating clock signals and the multiplexed transducer scanning signals, and for processing plural sequences of corrected or uncorrected flaw echo pulses and respective back echo pulses under control of the multiplexed transducer scanning signals and the workpiece position signal, thereby to produce arrays of multilevel, priority-encoded, defect signals rippled to an output which will aid a computer in workpiece flaw area reconstruction; and (f) said pulse-echo tester means including:
1. a search unit having a multichannel array of ultrasonic transducers, each transducer acoustically coupled to a different lateral incremental area of the workpiece;
2. an adjustable supply and return sources of ultrasound fluid for providing the transducer acoustical coupling and a coolant to a hot workpiece; and
3. workpiece temperature sensor and controller means for automatically adjusting the fluid supply to maintain a known value related to workpiece cooling and effect of temperature on acoustical coupling.

10. An ultrasonic inspection system for determining area defects in a flat workpiece movable along an inspection path and which may be subject to one or more error-causing variations in test conditions including workpiece alloy or composition, temperature, thickness and transducer gap, said system comprising:

(a) pulse-echo tester means producing a source of multi-channel ultrasonic echo pulses having a preset gain and output in corresponding sequences of front echo, flaw echo and back echo pulses per sequence from an array of transducers, said echo pulses derived from multiplexed transducer scanning signals causing testing of lateral incremental areas of the workpiece, each said echo pulse susceptible to one or more test error corrections;

(b) modifiable ultrasonic instrument means producing a single-channel sequence of front echo, flaw echo and back echo gates and outputting corresponding front echo, flaw echo and back echo gated pulses per sequence, said output derived from multiplexing each multi-channel testing of lateral incremental areas of the workpiece in response to the scanning signals;

(c) when desired, calibration means including controller means acting on a modified ultrasonic instrument and in response to a multiplexed sequence of said echo pulses and a preset reference signal for correcting echo pulse error proportional to one or more of said transducer-detected test condition variables causing said error;

(d) means for producing a position signal representing workpiece location at each lateral incremental area tested along the inspection path;

(e) multi-channel ultrasonic data buffer/controller means interconnectable with said ultrasonic instrument for generating clock signals and the multiplexed transducer scanning signals, and for processing plural sequences of corrected or uncorrected flaw echo pulses and respective back echo pulses under control of the multiplexed transducer scanning signals and the workpiece position signal, thereby to produce arrays of multi-level, priority-encoded, defect signals rippled to an output; and (f) digital processing means including a computer and terminal interactable with the multi-channel ultrasonic data buffer/controller, the multi-channel, multi-level, priority-encoded defect output signals, and the workpiece position signal for workpiece flaw area reconstruction, and if desired, further including means for producing one or more types of printouts of an encoded flaw area map and an encoded flaw area evaluation relative test position of the workpiece; and (g) said pulse-echo tester means including:
1. a search unit having a multi-channel array of ultrasonic transducers, each transducer acoustically coupled to a different lateral incremental area of the workpiece; and
2. an adjustable supply and return sources of ultrasound fluid for providing the transducer acoustical coupling and a coolant to a hot workpiece; and
3. workpiece temperature sensor and controller means for automatically adjusting the fluid supply to maintain a known value related to workpiece cooling and effect of temperature on acoustical coupling.

11. In an ultrasonic inspection system for determining area defects in a flat workpiece movable along an inspection path and which may be subject to one or more error-causing variable test conditions, said system including multi-channel ultrasonic pulse-echo tester means, and when desired, multi-channel calibration means for correcting a transducer-detected error, both means responsive to a multiplexed array of transducers signaled by transducer scanning signals, said tester means outputting plural sequences of front echo, flaw echo and back echo gated pulses per sequence derived from multiplexed testing of lateral incremental areas of the workpiece, each said echo pulse susceptible of one or more test error corrections, there also being means for producing a position signal representing workpiece location at each lateral incremental area tested along the inspection path, said system further including:

(a) digital multi-channel ultrasonic data buffer/controller means interconnectable with said ultrasonic instrument for generating clock signals and the multiplexed transducer scanning signals, and for processing plural sequences of corrected or uncorrected flaw echo pulses and respective back echo pulses under control of the transducer scanning signals, a preset reference signal, and the workpiece position signal, thereby to produce arrays of multi-level, priority-encoded, defect signals rippled to an output which will aid a computer in workpiece flaw area reconstruction; and (b) wherein the multi-channel calibration means which corrects the echo pulses for transducer-detected test error includes:
1. digital multi-channel automatic attenuation controller means acting in response to the multiplexed sequence of said echo pulses and a preset reference signal for correcting each echo pulse attenuation error, said controller means varying preset output gain proportional to attenuation error caused by each test transducer detecting one or more test condition variables including workpiece alloy or composition and temperature, said controller means outputting to a modified input of the ultrasonic instrument attenuation-error corrected front, flaw and back echo pulses;
2. digital automatic flaw gate range controller means acting in response to the multiplexed sequence of said attenuation corrected echo pulses and a preset reference signal for correcting each flaw echo pulse timing error, said controller means varying preset flaw gate off-time in a feedback loop to a further modified ultrasonic instrument proportional to timing error caused by each test transducer detecting one or more test condition variables including workpiece thickness and transducer gap, said controller means causing the ultrasonic instrument to output a timing-error corrected flaw echo pulse; and
3. whereby both controller means cause the ultrasonic instrument to output each sequence with attenuation-corrected front, flaw and back echo pulses, and a timing-error corrected flaw echo pulse in each sequence, both being processed by the multi-channel ultrasonic data buffer/controller means.

12. An ultrasonic inspection system for determining area defects in a flat workpiece movable along an inspection path and which may be subject to one or more error-causing variations in test conditions including workpiece alloy or composition, temperature, thickness and transducer gap, said system comprising:
(a) pulse-echo tester means producing a source of multi-channel ultrasonic echo pulses having a preset gain and output in corresponding sequences of front echo, flaw echo and back echo pulses per sequence from an array of transducers, said echo pulses derived from multiplexed transducer scanning signals causing testing of lateral incremental areas of the workpiece, each said echo pulse susceptible to one or more test error corrections;
(b) modifiable ultrasonic instrument means producing a single-channel sequence of front echo, flaw echo and back echo gates and outputting corresponding front echo, flaw echo and back echo gated pulses per sequence, said output derived from multiplexing each multi-channel testing of lateral incremental areas of the workpiece in response to the scanning signals;
(c) when desired, calibration means including controller means acting on a modified ultrasonic instrument and in response to a multiplexed sequence of said echo pulses and a preset reference signal for correcting echo pulse error proportional to one or more of said transducer-detected test condition variables causing said error;
(d) means for producing a position signal representing workpiece location at each lateral incremental area tested along the inspection path;
(e) multi-channel ultrasonic data buffer/controller means interconnectable with said ultrasonic instrument for generating clock signals and the multiplexed transducer scanning signals, and for processing plural sequences of corrected or uncorrected flaw echo pulses and respective back echo pulses under control of the multiplexed transducer scanning signals and the workpiece position signal, thereby to produce arrays of multi-level, priority-encoded, defect signals rippled to an output which will aid a computer in workpiece flaw area reconstruction; and
(f) the calibration means (c) includes:
1. digital multi-channel automatic attenuation controller means acting in response to the multiplexed sequence of said echo pulses and a preset reference signal for correcting each echo pulse attenuation error, said controller means varying preset output gain proportional to attenuation error caused by each test transducer detecting one or more test condition variables including workpiece alloy or composition and temperature, said controller means outputting to a modified input of the ultrasonic instrument attenuation-error corrected front, flaw and back echo pulses;
2. digital automatic flaw gate range controller means acting in response to the multiplexed sequence of said attenuation corrected echo pulses and a preset reference signal for correcting each flaw echo pulse timing error, said controller means varying preset flaw gate off-time in a feedback loop to a further modified ultrasonic instrument proportional to timing error caused by each test transducer detecting one or more test condition variables including workpiece thickness and transducer gap, said controller means causing the ultrasonic instrument to output a timing-error corrected flaw echo pulse; and
3. whereby both controller means cause the ultrasonic instrument to output each sequence with attenuation-corrected front, flaw and back echo pulses, and a timing-error corrected flaw echo pulse in each sequence, both being processed by the multi-channel ultrasonic data buffer/controller means.

13. An ultrasonic inspection system for determining area defects in a flat workpiece movable along an inspection path and which may be subject to one or more error-causing variations in test conditions including workpiece alloy or composition, temperature, thickness and transducer gap, said system comprising:
(a) pulse-echo tester means producing a source of multi-channel ultrasonic echo pulses having a preset gain and output in corresponding sequences of front echo, flaw echo and back echo pulses per sequence from an array of transducers, said echo pulses derived from multiplexed transducer scanning signals causing testing of lateral incremental areas of the workpiece, each said echo pulse susceptible to one or more test error corrections;
(b) modifiable ultrasonic instrument means producing a single-channel sequence of front echo, flaw echo and back echo gates and outputting corresponding front echo, flaw echo and back echo gated pulses per sequence, said output derived from multiplexing each multi-channel testing of lateral incremental areas of the workpiece in response to the scanning signals;

(c) when desired, calibration means including controller means acting on a modified ultrasonic instrument and in response to a multiplexed sequence of said echo pulses and a preset reference signal for correcting echo pulse error proportional to one or more of said transducer-detected test condition variables causing said error;

(d) means for producing a position signal representing workpiece location at each lateral incremental area tested along the inspection path;

(e) multi-channel ultrasonic data buffer/controller means interconnectable with said ultrasonic instrument for generating clock signals and the multiplexed transducer scanning signals, and for processing plural sequences of corrected or uncorrected flaw echo pulses and respective back echo pulses under control of the multiplexed transducer scanning signals and the workpiece position signal, thereby to produce arrays of multi-level, priority-encoded, defect signals rippled to an output;

(f) digital processing means including a computer and terminal interactable with the multi-channel ultrasonic data buffer/controller, the multi-channel, multi-level, priority-encoded defect output signals, and the workpiece position signal for workpiece flaw area reconstruction, and if desired, further including meand for producing one or more types of printouts of an encoded flaw area map and an encoded flaw area evaluation relative test position of the workpiece; and (g) the calibration means (c) includes:
1. digital multi-channel automatic attenuation controller means acting in response to the multiplexed sequence of said echo pulses and a preset reference signal for correcting each echo pulse attenuation error, said controller means varying preset output gain proportional to attenuation error caused by each test transducer detecting one or more test condition variables including workpiece alloy or composition and temperature, said controller means outputting to a modified input of the ultrasonic instrument attenuation-error corrected front, flaw and back echo pulses;
2. digital automatic flaw gate range controller means acting in response to the multiplexed sequence of said attenuation corrected echo pulses and a preset reference signal for correcting each flaw echo pulse timing error, said controller means varying preset flaw gate off-time in a feedback loop to a further modified ultrasonic instrument proportional to timing error caused by each test transducer detecting one or more test condition variables including workpiece thickness and transducer gap, said controller means causing the ultrasonic instrument to output a timing-error corrected flaw echo pulse; and
3. whereby both controller means cause the ultrasonic instrument to output each sequence with attenuation-corrected front, flaw and back echo pulses, and a timing-error corrected flaw echo pulse in each sequence, both being processed by the multi-channel ultrasonic data buffer/controller means.

14. In an ultrasonic inspection system for determining area defects in a flat workpiece movable along an inspection path and which is subject to one or more error-causing variable test conditions, said system including multi-channel ultrasonic pulse-echo tester means and calibration means for correcting a transducer-detected echo-pulse error, both responsive to a multiplexed array of transducers signaled by transducer scanning signals, said tester means having an ultrasonic instrument outputting plural sequences of front echo, flaw echo and back echo gated pulses per sequence derived from multiplexed testing of lateral incremental areas of the workpiece, there also being means for producing a position signal representing workpiece location at each lateral incremental area tested along the inspection path, as well as multi-channel ultrasonic data buffer/controller means for generating clock signals and the scanning signals and for processing arrays of multi-channel lateral area flaw echo pulses and respective back echo pulses under control of the scanning signals and the workpiece position signal, said calibration means including:

(a) digital multi-channel automatic attenuation controller means acting in response to the multiplexed sequence of said echo pulses and a preset reference signal for correcting each echo pulse attenuation error, said controller means varying preset output gain proportional to attenuation error caused by each test transducer detecting one or more test condition variables including workpiece alloy or composition and temperature, said controller means outputting to a modified input of the ultrasonic instrument attenuation-error corrected front, flaw and back echo pulses, the corrected flaw and back echo pulses also used in the multi-channel ultrasonic data buffer/controller means;

(b) means for presetting workpiece echo pulse zero attenuation and back echo pulse reference attenuation preset signals;

(c) clocked digital echo pulse processing means logically controlled in response to the attenuation preset signals, the multiplex scanning signals and a digital back echo pulse of each sequence for sequentially determining and storing multi-channel calculated attenuation correction factors relative the attenuation preset signals, one such factor for every sequence scanned which is proportional to the one or more transducer-detected attenuation errors; and (d) attenuator means for receiving at an input the sequence of uncorrected echo pulses, for varying preset output gain thereof based on a stored calculated attenuation correction factor for the corresponding channel scanned, and for outputting said attenuation-error corrected front, flaw and back echo pulse sequence.

15. The system of claim 14 wherein the echo pulse processing means determines the stored calculated attenuation correction factor by a comparison of the digital back echo pulse of each sequence with the preset back echo pulse reference attenuation signal to obtain a difference thereof, said difference ratioed with the preset echo pulse zero attenuation signal as a basis for representing said correction factor.

16. The system of claim 15 further including converter means for converting a digital calculated attenuation correction factor into an analog form applied to the output attenuator means.

17. The system of claim 14 further including display means for displaying the calculated attenuation correction factor and, if desired, a preselected transducer channel number in response to a channel selector signal source.

18. In an ultrasonic inspection system for determining defects in a flat workpiece movable along an inspection path and which is subject to one or more error-causing variable test conditions, said system including multi-channel ultrasonic pulse-echo tester means and calibration means for correcting a transducer-detected echo-pulse error, both responsive to a multiplexed array of transducers signaled by transducer scanning signals, said tester means having an ultrasonic instrument outputting plural sequences of front echo, flaw echo and back echo gated pulses per sequence derived from multiplexed testing of lateral incremental areas of the workpiece, there also being means for producing a position signal representing workpiece location at each lateral incremental area tested along the inspection path, as well as multi-channel ultrasonic data buffer/controller means for generating clock signals and the scanning signals and for processing arrays of multi-channel lateral area flaw echo pulses and respective back echo pulses under control of the scanning signals and the workpiece position signal, said calibration means including:
 (a) digital automatic flaw gate range controller means acting in response to the multiplexed sequence of said echo pulses and a preset reference signal for correcting each flaw echo pulse timing error, said controller means varying preset flaw gate off-time in a feedback loop to a modified ultrasonic instrument proportional to timing error caused by each test transducer detecting one or more test condition variables including workpiece thickness and transducer gap, said controller means causing the ultrasonic instrument to output a timing-error corrected flaw echo pulse to the multi-channel ultrasonic data buffer/controller means;
 (b) means for presetting flaw gate zero echo time and reference echo time signals related to workpiece thickness,
 (c) clocked digital echo pulse processing means logically controlled in response to the flaw gate timing preset signals and a sequence of front and back echo pulses for determining and storing a flaw gate turn-off signal relative the timing preset signals at the end of each sequence, said flaw gate turn-off signal varying beyond the preset reference echo time signal proportional to the echo time difference between the actual front and back echo pulses, which time difference is proportional to the one or more transducer-detected timing errors; and
 (d) means for outputting the flaw gate off-time signal in a feedback loop to a modified flaw gate in the ultrasonic instrument so that said instrument outputs a timing-error flaw echo pulse and a back echo pulse to the multi-channel ultrasonic data buffer/controller means.

19. The system of claim 18 wherein the digital echo pulse processing means includes logic means and counter means responsive to the front and back echo pulses and the preset signals, said counter means having a gate range counter producing and storing the flaw gate turn-off signal at the end of each sequence.

20. The system of claim 19 wherein the counter means further includes in series combination a zero decrement counter acted on by the zero echo time preset signal, a calibration counter passing decrement counter output under control of the logic means, complementing multiplexers acted on by the preset reference echo time signal for controlling calibration counter output to the flaw gate ranging counter to represent the variable flaw gate turn-off signal.

21. In an ultrasonic inspection system for determining area defects in a flat workpiece movable along an inspection path and which may be subject to one or more error-causing variable test conditions, said system including multi-channel ultrasonic pulse-echo tester means, and when desired, multi-channel calibration means for correcting a transducer-detected error, both means responsive to a multiplexed array of transducers signaled by transducer scanning signals, said tester means outputting plural sequences of front echo, flaw echo and back echo gated pulses per sequence derived from multiplexed testing of lateral incremental areas of the workpiece, each said echo pulse susceptible of one or more test error corrections, there also being means for producing a position signal representing workpiece location at each lateral incremental area tested along the inspection path, said system further including:
 (a) digital multi-channel ultrasonic data buffer/controller means interconnectable with said ultrasonic instrument for generating clock signals and the multiplexed transducer scanning signals, and for processing plural sequences of corrected or uncorrected flaw echo pulses and respective back echo pulses under control of the transducer scanning signals, a preset reference signal, and the workpiece position signal, thereby to produce arrays of multi-level, priority-encoded, defect signals rippled to an output which will aid a computer in workpiece flaw area reconstruction;
 (b) clock means for generating the clock signals and the multiplexed transducer scanning signals;
 (c) digital means for presetting maximum and minimum flaw echo reference signals;
 (d) clocked multi-channel means responsive to the preset reference signals and the scanning signals for converting each sequence of corrected or uncorrected flaw echo pulse and a respective back echo pulse from the ultrasonic instrument into one of plural stored arrays of multi-channel, multi-level, priority-encoded defect signals, one such defect signal for each incremental area forming a lateral strip on the workpiece multiplexed by the scanning signal, each stored array being rippled through storage means under control of the workpiece position signal to a multi-channel output; and
 (e) output means for communicating rippled arrays of multi-channel, priority-encoded, defect signals to external digital processing means to aid in workpiece flaw area reconstruction.

22. The system of claim 21 wherein the multi-channel converting means produces the stored arrays of multi-channel, multi-level, priority-encoded, defect signals by ratioing digital values of each flaw echo pulse with respective back echo pulses, comparing said ratio signal with maximum and minimum preset flaw echo reference signals, priority encoding each said comparison signal at one of plural levels of defect severity, and storing single and plural arrays of multi-channel defect signals so obtained.

* * * * *